US008470808B2

(12) United States Patent
Piganelli et al.

(10) Patent No.: US 8,470,808 B2
(45) Date of Patent: Jun. 25, 2013

(54) OXIDANT SCAVENGERS FOR TREATMENT OF TYPE I DIABETES OR TYPE II DIABETES

(76) Inventors: Jon D. Piganelli, Pittsburgh, PA (US); Kathryn Haskins, Denver, CO (US); Sonia C. Flores, Denver, CO (US); James D. Crapo, Denver, CO (US); Brian J. Day, Denver, CO (US); Ronald G. Gill, Denver, CO (US); Richard Gammans, Mission Viejo, CA (US); Manisha Patel, Denver, CO (US)

( * ) Notice: Subject to any disclaimer, the term of this patent is extended or adjusted under 35 U.S.C. 154(b) by 191 days.

(21) Appl. No.: 12/941,933

(22) Filed: Nov. 8, 2010

(65) Prior Publication Data
US 2011/0105452 A1    May 5, 2011

Related U.S. Application Data

(60) Continuation of application No. 11/857,949, filed on Sep. 19, 2007, now abandoned, which is a continuation of application No. 10/159,280, filed on Jun. 3, 2002, now abandoned, which is a continuation-in-part of application No. 11/424,662, filed on Jun. 16, 2006, which is a division of application No. 10/349,171, filed on Jan. 23, 2003, which is a continuation of application No. 09/490,537, filed on Jan. 25, 2000.

(60) Provisional application No. 60/328,398, filed on Oct. 12, 2001, provisional application No. 60/294,604, filed on Jun. 1, 2001, provisional application No. 60/117,010, filed on Jan. 25, 1999.

(51) Int. Cl.
*A61K 31/555* (2006.01)
*A61K 31/40* (2006.01)

(52) U.S. Cl.
USPC .......................... 514/185; 514/410; 514/866

(58) Field of Classification Search
USPC .......................................... 514/185, 410, 866
See application file for complete search history.

(56) References Cited

U.S. PATENT DOCUMENTS

| | | |
|---|---|---|
| 2,951,799 A | 9/1960 | Sharp |
| 4,614,723 A | 9/1986 | Schmidt |
| 4,657,902 A | 4/1987 | Kappas et al. |
| 4,746,735 A | 5/1988 | Kruper, Jr. et al. |
| 4,758,422 A | 7/1988 | Quay |
| 4,829,984 A | 5/1989 | Gordon |
| 4,837,221 A | 6/1989 | Bonnett |
| 4,851,403 A | 7/1989 | Picker et al. |
| 4,861,760 A | 8/1989 | Mazuel et al. |
| 4,866,054 A | 9/1989 | Dori et al. |
| 4,885,114 A | 12/1989 | Gordon et al. |
| 4,892,941 A | 1/1990 | Dolphin et al. |
| 4,895,719 A | 1/1990 | Radhakrishnam |
| 4,911,920 A | 3/1990 | Jani et al. |
| 4,963,367 A | 10/1990 | Ecanow |
| 5,010,073 A | 4/1991 | Kappas et al. |
| 5,051,337 A | 9/1991 | Sakoda et al. |
| 5,087,438 A | 2/1992 | Gordon |
| 5,109,016 A | 4/1992 | Dixon et al. |
| 5,130,245 A | 7/1992 | Marklund et al. |
| 5,162,519 A | 11/1992 | Bonnett |
| 5,169,630 A | 12/1992 | Okaya et al. |
| 5,171,680 A | 12/1992 | Mullenbach et al. |
| 5,192,757 A | 3/1993 | Johnson et al. |
| 5,192,788 A | 3/1993 | Dixon et al. |
| 5,202,317 A | 4/1993 | Bruice |
| 5,212,162 A | 5/1993 | Missel et al. |
| 5,217,966 A | 6/1993 | Bruice |
| 5,223,538 A | 6/1993 | Fridovich |
| 5,227,405 A | 7/1993 | Fridovich |
| 5,236,914 A | 8/1993 | Meunier |
| 5,236,915 A | 8/1993 | Fiel |
| 5,248,603 A | 9/1993 | Marklund et al. |
| 5,262,532 A | 11/1993 | Tweedle et al. |
| 5,277,908 A | 1/1994 | Beckman et al. |
| 5,281,616 A | 1/1994 | Dixon et al. |
| 5,284,647 A | 2/1994 | Niedballa et al. |
| 5,366,729 A | 11/1994 | Marklund et al. |
| 5,403,834 A | 4/1995 | Malfroy-Camine et al. |
| 5,403,841 A | 4/1995 | Lang et al. |
| 5,405,369 A | 4/1995 | Selman et al. |
| 5,472,691 A | 12/1995 | Marklund et al. |
| 5,493,017 A | 2/1996 | Therien et al. |

(Continued)

FOREIGN PATENT DOCUMENTS

| | | |
|---|---|---|
| EP | 127797 A1 | 12/1984 |
| EP | 186962 A1 | 7/1986 |

(Continued)

OTHER PUBLICATIONS

Archibald et al., Investigations of the State of the Manganese in *Lactobacillus plantarum*, Archives of Biochemistry and Biophysics 215(2):589-596 (1982).
Archibald et al., Manganese and Defenses against Oxygen Toxicity in *Lactobacillus plantarum*, Journal of Bacteriology 145(1):442-451 (1981).
Archibald et al., Manganese, Superoxide Dismutase, Oxygen Tolerance in Some Lactic Acid Bacteria, Journal of Bacteriology 146(3):928-936 (1981).
Archibald et al., The Scavenging of Superoxide Radical by Manganous Complex: In Vitro, Archives of Biochemistry and Biophysics 214(2):452-463 (1982).
Balch, "Geometric and electronic structure and dioxygen sensitivity of the copper complex of octaethylbilindione, a biliverdin analog", J. Am. Chem. Soc. 115(25):12206-12207 (1993).
Balch, "Isolation and characterization of an iron biliverdin-type complex that is formed along with verdohemochrome during the coupled oxidation of iron (II) octaethylporphyrin", Am. Chem. Soc. 115(20):9056-9061 (1993).
Balch, "Solid-state self-association of the two-electron oxidation product of a biliverdin analogue", J. Chem. Soc. Chem. Commun. 6:643-644 (1995).

(Continued)

*Primary Examiner* — Kevin E Weddington
(74) *Attorney, Agent, or Firm* — Kilpatrick Townsend & Stockton LLP

(57) ABSTRACT

The present invention relates, in one embodiment, to a method of preventing or treating diabetes using low molecular weight antioxidants. In a further embodiment, the invention relates to a method of protecting and/or enhancing viability of cells/tissues/organs during isolation (harvesting), preservation, expansion and/or transplantation. In yet another embodiment, the present invention relates to a method of inducing immune tolerance. The invention also relates to compounds and compositions suitable for use in such methods.

9 Claims, 28 Drawing Sheets

U.S. PATENT DOCUMENTS

| | | | |
|---|---|---|---|
| 5,563,132 A | 10/1996 | Bodaness | |
| 5,599,924 A | 2/1997 | Thieren et al. | |
| 5,604,199 A | 2/1997 | Funanage | |
| 5,610,293 A | 3/1997 | Riley et al. | |
| 5,637,578 A | 6/1997 | Riley et al. | |
| 5,674,467 A | 10/1997 | Maier et al. | |
| 5,747,026 A | 5/1998 | Crapo | |
| 5,767,272 A | 6/1998 | Wijesekera et al. | |
| 5,834,509 A | 11/1998 | Malfroy-Camine et al. | |
| 5,874,421 A | 2/1999 | Riley et al. | |
| 5,948,771 A | 9/1999 | Danziger | |
| 5,976,498 A | 11/1999 | Neumann et al. | |
| 5,976,551 A | 11/1999 | Mottez et al. | |
| 5,994,339 A | 11/1999 | Crapo et al. | |
| 5,994,410 A | 11/1999 | Chiang et al. | |
| 6,013,241 A | 1/2000 | Marchal et al. | |
| 6,046,188 A | 4/2000 | Malfroy-Camine et al. | |
| 6,060,467 A | 5/2000 | Buelow et al. | |
| 6,084,093 A | 7/2000 | Riley et al. | |
| 6,087,493 A | 7/2000 | Wheelhouse et al. | |
| 6,103,714 A | 8/2000 | Fridovich et al. | |
| 6,127,356 A | 10/2000 | Crapo et al. | |
| 6,180,620 B1 | 1/2001 | Salvemini | |
| 6,204,259 B1 | 3/2001 | Riley et al. | |
| 6,214,817 B1 | 4/2001 | Riley et al. | |
| 6,245,758 B1 | 6/2001 | Stern et al. | |
| 6,372,727 B1 | 4/2002 | Crow et al. | |
| 6,395,725 B1 | 5/2002 | Salvemini | |
| 6,403,788 B1 | 6/2002 | Meunier et al. | |
| 6,417,182 B1 | 7/2002 | Abrams et al. | |
| 6,479,477 B1 | 11/2002 | Crapo et al. | |
| 6,544,975 B1 | 4/2003 | Crapo et al. | |
| 6,548,045 B2 | 4/2003 | Sakata et al. | |
| 6,566,517 B2 | 5/2003 | Miura et al. | |
| 6,573,258 B2 | 6/2003 | Bommer et al. | |
| 6,583,132 B1 | 6/2003 | Crapo et al. | |
| 6,602,998 B2 | 8/2003 | Kobuke et al. | |
| 6,624,187 B1 | 9/2003 | Pandey et al. | |
| 6,916,799 B2 | 7/2005 | Fridovich et al. | |
| 7,189,707 B2 * | 3/2007 | Crapo et al. | 514/185 |
| 7,470,677 B2 | 12/2008 | Crapo et al. | |
| 7,820,644 B2 | 10/2010 | Crapo et al. | |
| 2002/0042407 A1 | 4/2002 | Fridovich et al. | |
| 2002/0058643 A1 | 5/2002 | Cherian et al. | |
| 2007/0149498 A1 | 6/2007 | Crapo et al. | |
| 2007/0197496 A1 | 8/2007 | Crapo et al. | |

FOREIGN PATENT DOCUMENTS

| | | |
|---|---|---|
| EP | 282899 A2 | 9/1988 |
| EP | 0 284 645 A2 | 10/1988 |
| EP | 336879 A1 | 10/1989 |
| EP | 337601 A1 | 10/1989 |
| EP | 345171 A1 | 12/1989 |
| EP | 414915 A1 | 3/1991 |
| EP | 462836 A2 | 12/1991 |
| EP | 524161 A1 | 1/1993 |
| EP | 532327 A2 | 3/1993 |
| EP | 1616869 A1 | 1/2006 |
| FR | 2676738 A1 | 11/1992 |
| JP | 02-289844 | 11/1990 |
| JP | 3273082 | 12/1991 |
| WO | WO 91/04315 A1 | 4/1991 |
| WO | WO 91/19977 A1 | 12/1991 |
| WO | WO 92/07935 A1 | 5/1992 |
| WO | WO 92/08482 A1 | 5/1992 |
| WO | WO 92/15099 A1 | 9/1992 |
| WO | WO 93/02090 A1 | 2/1993 |
| WO | WO 94/04614 | 3/1994 |
| WO | WO 94/05285 A1 | 3/1994 |
| WO | WO 94/24116 | 10/1994 |
| WO | WO 95/10185 A1 | 4/1995 |
| WO | WO 95/31197 A1 | 11/1995 |
| WO | WO 96/09038 A2 | 3/1996 |
| WO | WO 96/09053 A1 | 3/1996 |
| WO | WO 96/40148 A1 | 12/1996 |
| WO | WO 96/40223 A1 | 12/1996 |
| WO | WO 97/06824 A2 | 2/1997 |
| WO | WO 97/06830 A1 | 2/1997 |
| WO | WO 97/06831 A1 | 2/1997 |
| WO | WO 97/33588 A1 | 9/1997 |
| WO | WO 97/33877 A1 | 9/1997 |
| WO | WO 98/33503 A1 | 8/1998 |
| WO | WO 98/58636 A1 | 12/1998 |
| WO | WO 99/07687 | 2/1999 |
| WO | WO 99/10317 | 3/1999 |
| WO | WO 99/23097 A1 | 5/1999 |
| WO | WO 99/55388 A1 | 11/1999 |
| WO | WO 00/04868 A2 | 2/2000 |
| WO | WO 00/19993 A2 | 4/2000 |
| WO | WO 00/23568 A2 | 4/2000 |
| WO | WO 00/43395 A1 | 7/2000 |
| WO | WO 00/72893 A2 | 12/2000 |
| WO | WO 00/75144 A2 | 12/2000 |
| WO | WO 01/26655 A1 | 4/2001 |
| WO | WO 01/96345 A1 | 12/2001 |
| WO | WO 02/04454 A1 | 1/2002 |
| WO | 02/060383 A2 | 8/2002 |
| WO | 02/078670 A1 | 10/2002 |
| WO | WO 02/096366 A2 | 12/2002 |
| WO | 2011/028935 A2 | 3/2011 |

OTHER PUBLICATIONS

Bamford et al., "The Squalestatins: Synthesis and Biological Activity of Some C3-Modified Analogues; Replacement of a Carboxylic Acid or Methyl Ester with an Isoelectric Heterocyclic Functionality", J. Med. Chem. 38:3502-3513 (1995).

Batinic-Haberle et al, "Manganese(ill) meso-tetrakis(ortho-N-alkylpyridyl)porphyrins. Synthesis, characterization, and catalysis of 02.- dismutation", J. Chem. Soc. Dalton Trans., pp. 2689-2696 (2002).

Batinic-Haberle et al, Relationship among Redox Potentials, proton Dissociation Constants of Pyrrolic Nitrogens, and in Vivo and in Vitro Superoxide Dismutating Activities of Manganese(III) and Iron(III) Water-Soluble Porphyrins Inorg. Chem. 38:4011-4022 (1999).

Batinic-Haberle et al, "The Ortho Effect Makes Manganic Meso-Tetrakis-(N-Methylpyridinium-2-YL)(MnTM-2-PyPs+) A Powerful and Useful Superoxide Dismutase Mimic", Oxygen '97, The 4th Annual Meeting of the Oxygen Society, Council Meeting, The Palace Hotel, San Francisco, California, Nov. 20-24, 1997,—p. 38, Abstract 1-8.

Batinic-Haberle et al., "A Potent Superoxide Dismutase Mimic" Manganese[B]-Octabromo-meso-tetrakis (Nmethylpyridinium-4-yl)Porphyrin, Archives of Biochemistry and Biophysics 343(2):225-233 (1997).

Baudry et al., "Salen-Manganese Complexes are Superoxide Dismutase-Mimics", Biochemical and Biophysical Research Communication 192(2):964-968 (1993).

Beckman et al, "Apparent hydroxyl radical production by peroxynitrite: Implications for endothelial injury from nitric oxide and superoxide", Proc. Natl. Acad. Sci. USA 87:1620-1624 (1990).

Bedioui et al., "Metalloporphyrin-Polypyrrole Film Electrode: Characterization and Catalytic Application", J. Electroanal. Chem. 207:87-99 (1986).

Beil et al, "Helicobacter pylori Reduces intracellular Glutathione in Gastric Epithelial Cells", Digestive Diseases and Sciences 45(9):1769-1773 (2000).

Berezin et al, Effect of ligand structure on the kinetic stability of tetraphenylporphyrin complexes of zinc and cadmium, Zhurnal Neorganicheskoi Khimii 25(10):2645-2652 (1980).

Berezin et I, "Factors determining the stability of complexes of copper with p-substituted derivatives of tetraphenylporphine", Zhurnal Fizicheskoi Khimil 53(11 ):2716-2719 (1979)—English Abstract.

Beyer, Jr., Characterization of a Superoxide Dismutase Mimic Prepared from Desferrioxamine and Mn02, Archives of Biochemistry and Biophysics 271(1):149-156 (1989).

Bishop et al., "The Reaction of Thiomides with Phosphorus Ylides", J. Org. Chem. 56:5079-5091 (1991).

Bloodsworth et al, "Manganese-Porphyrin Reactions with Lipids and Lipoproteins", Free Radical Biology & Medicine 28(7):1017-1029 (2000).

Bockhorst and Hoehn-Berlage, "An Optimized Synthesis of Manganese meso-Tetra(4-sulfonato phenyl) porphine: A Tumor-Selective MRI Contrast Agent", Tetrahedron 50(29):8657-8660 (1994).
Boissinot et al., "Rational Design and Expression of a Heparin-Targeted Human Superoxide Dismutase", Biochemical and Biophysical Research Communication 190(1):250-256 (1993).
Bors et al., "An expanded function for superoxide dismutase", Chemical Abstracts 115:388 (1991), Abstract No. 109185h.
Bottino, Rita et al., "Preservation of human islet cell functional mass by anti-oxidative action of a novel SOD mimic compound", Diabetes, 51:2561-7, Aug. 2002.
Brigelius et al., "Superoxide Dismutase Activity of Low Molecular Weight Cu2+—Chelates Studied by Pulse Radiolysis", FEBS Letters 47(1):72-75 (1974).
Burke, "Photochemical and thermal transformations of phytochrome", Chem. Physiol. Bile Pigm., Int. Symp., pp. 509-517 (1975).
Butje et al., "Electronic Spectra, Resonance Raman Spectra and Solution Properties of Water-soluble (Cu(II), Ni(II) and Co(III) Porphyrins", Inorg. Chim. Acta 167:97-108 (1990).
Callot and Schaeffer, "Ring contraction of homoporphyrins to porphyrins, meso-Reactivity of 5,10,15Triphenylporphin and Porphin", J. Chem. Research (S):51 (1978).
Chung et al, "Protective effects of heroin and tetrakis(4-benzoic acid)porphyrin on bacterial mutagenesis and mouse skin carcinogenesis induced by 7,12-dimethylbenz[a]anthracene", Mutation Research 472:139-145 (2000).
Clyde et al., "Distribution of Manganese Superoxide Dismutase mRNA in Normal and Hyperoxic Rat Lung", American Journal of Respiratory Cell and Molecular Biology 8:530-537 (1993).
Collman et al., "Synthesis of "Face to Face" Porphyrin Dimers Linked by 5,15-Substituents: Potential Binuclear Multielectron Redox Catalysts", J. Am. Chem. Soc. 103:516-533 (1981).
Comhair et al., "Rapid loss of superoxide dismutase activity during antigen-induced asthmatic response", Lancet 355 (9204):624 (2000).
Crapo and Tierney "Superoxide dismutase and pulmonary oxygen toxicity", Am. J. Physiol. 226:1401-1407 (1974).
Crapo et al., "Superoxide Dismutase and Oxygen Toxicity", Clinical Research, p. 222, 1991.
Crapo et al., "The Failure of Aerosolized Superoxide Dismutase to Modify Pulmonary Oxygen Toxicity", American Review of Respiratory Disease 115:1027-1033 (1977).
Crapo et al., 721195, Document No. 123:218443 (1994).
Darr et al., "A Mimic of Superoxide Dismutase Activity Based Upon Desferrioxamine B and Manganese(IV)", Archives of Biochemistry and Biophysics 258(2):351-355 (1987).
Datta-Gupta et al., "Synthetic Porphyrins II Preparation and Spectra of Some Metal Chelates of para", Journal of Substituted-mesa-TetraDhenylporphines, J. of Pharmaceutical Science 57(2):300-304 (1968).
Datta-Gupta et al., "Synthetic Porphyrins. I. Synthesis and Spectra of Some para-Substituted mesoTetraphenylporphines (1)", J. Heterocycl. Chem. 3:495-502 (1966).
Davila et al., "Sterically-Hindered Zinc Porphyrins for Solar-Energy Conversion", J. Chem. Soc., Chem. Commun., pp. 525-527 (1987).
Day et al., "A Metalloporphyrin Superoxide Dismutase Mimetic Protects Against Paraquat-Induced Endothelial Cell Injury, in Vitro", The Journal of Pharmacology and Experimental Therapeutics 275(3):1227-1232 (1995).
Day et al., "Manganic Porphyrins Possess Catalase Activity . . . ," Arch. Biochem. Biophys., vol. 347, No. 2, pp. 256-262 (1997).
De Peretti et al., "Imidazol[2,1-b]benzoxazole-3-acetamide derivatives, their preparation, and their therapeutic use", Chemical Abstracts 121:1016, Abstract No. 121:200896u, 1996.
Dealvare et al., "Mechanism of Superoxide Anion Scavenging Reaction by Bis-(Salicylato)-Copper(II) Complex", Biochemical and Biophysical Research Communications 69(3):687-694 (1976).
Deune et al., "Prevention of Ischemia-Reperfusion Injury with a Synthetic Metalloprotein Superoxide Dismutase Mimic, SC52608", Plastic and Reconstructive Surgery 98(4):711-718 (1996).
Diguiseppi et al., "Putative Superoxide Dismutase Activity of Iron-EDTA: A Reexamination", Archives of Biochemistry and Biophysics 203(1):145-150 (1980).

Dwyer et al., "Protective Properties of Tin- and Manganese-Centered Porphyrins Against Hydrogen PeroxideMediated Injury in Rat Astroglial Cells", J. Neurochem 71:2497 (1998).
Elangovan and Krishnan, "Photophysical properties of porphyrin amphiphiles bearing pyridinium alkyl groups", Chemical Physics Letters 194(1,2):139-146 (1992), XP000986304.
El-Far and Pimstone, "Selective in Vivo Tumor Localization of Uroporphyrin Isomer I in Mouse Mammary Carcinoma: Superiority over Other Porphyrins in a Comparative Study", Cancer Research 46:34390-4394 (1986).
Epp et al., "Superoxide Dismutase Activity of Manganese Chelates", 76-78 (1986).
Fajer et al., "Tr-Cation Radicals and Dications of Metalloporphyrins", Journal of the American Chemical Society 92 (11):3451-3459 (1970).
Falk, "Contributions to the chemistry of pyrrolic pigments", Tetrahedron 37(4):761-7 (1981).
Faulkner et al., "Characterization of Mn(III) Complexes of Linear and Cyclic Desferrioxamines as Mimics of Superoxide Dismutase Activity", Archives of Biochemistry and Biophysics 310(2):341-346 (1994).
Faulkner et al., Stable Mn(III) Porphyrins Mimic Superoxide Dismutase in Vitro and Substitute for It in Vivo, The Journal of Biological Chemistry 269(38):23471-23476 (1994).
Folz et al., "Extracellular Superoxide Dismutase (SODS): Tissue-Specific Expression, Genomic Characterization, and Computer-Assisted Sequence Analysis of the Human EC SOD Gene", Genomics 22:162-171 (1994).
Foran et al., "Effect of Electrolyte Concentration on Axial Anion Ligation in Manganese(III) mesa Tetraphenylporphyrin Chlorides", Inorg. Chem. 31:1463-1470 (1992).
Gassman et al., "Electronic Effects of Peripheral Substituents in Porphyrins: X-ray Photoelectron Spectroscopy and ab Initio Self-Consistent Field Calculations", J. Am. Chem. Soc. 114:9990-10000 (1992).
Gauuan et al, "Superoxide dismutase mimetics: synthesis and structure-activity relationship study of MnTBAP analogues", Bioorganic & Medicinal Chemistry 10(9):3013-3021 (2002).
Ghosh, "Substituent Effects on Valence Ionization Potentials of Free Base Porphyrins: Local Density Functional Calculations and Their Relevance to Electrochemical and Photoelectron Spectroscopic Studies", J. Am. Chem. Soc. 117:4691-4699 (1995).
Giraudeau et al., "Substituent Effects in the Electroreduction of Porphyrins and Metalloporphyrins", Journal of the American Chemical Society 101(14):3857-3862 (1979).
Gonzalez et al., "EUK-8, a Synthetic Superoxide Dismutase and Catalase Mimetic, Ameliorates Acute Lung Injury in Endotexemic Swine", The Journal of Pharmacology and Experimental Therapeutics 275(2):798-806 (1995).
Groves and Marla, "Peroxynitrite-Induced DNA Strand Scission Mediated by a Manganese Porphyrin", J. Am. Chem. Soc. 117(37):9578-9579 (1995).
Halliwell, Barry, "The Superoxide Dismutase Activity of Iron Complexes", FEBS Letters 56(1):34-38 (1975).
Hambright et al, "Synthesis and Characterization of New Isomeric Water-Soluble Porphyrins Tetra(2-Nmethylpyridyl)porphine and Tetra(3-N-methylpyridyl)porphine", Inorganic Chemistry 15(9):2314-2315 (1976).
Hambright et al, "An acid solvolysis kinetic study of manganese(II)-tetra(2-N-methylpyridyl)porphine", J. Inorg. Chem. 39:1102-1103 (1977).
Hambright et al., "Manganese(III) porphyrin isomers: polarography and stannous ion reduction kinetics", Porphyrin Chem. Adv., editor: Longo, [Pap. Porphyrin Symp.], pp. 284-292, Meeting Date 1977.
Harriman et al., "Photochemistry of Manganese Porphyrins Part 2.-Photoreduction", pp. 1543-1552, 1998.
Harriman et al., "Photochemistry of Manganese Porphyrins", J. Chem. Soc. 275:1532-1542 (1979).
Hunt et al., "Amphiphilic peroxynitrite decomposition catalysts in liposomal assemblies", Chemistry & Biology 4 (11):845-858 (1997).
Ilan et al., "Superoxide Dismuting Activity of an Iron Porphyrin", Inorg. Nucl. Chem. Letters 17(3/4):93-96 (1981) Couple, J. Phys. Chem. 86:1842-1849 (1982).

Inoue et al., "Expression of a Hybrid Cu/Zn-type Superoxide . . . ," J. Bio. Chem., vol. 266, No. 25, pp. 16409-16414 (1991).
International Search Report and Written Opinion from corresponding Application No. PCT/US00/02062 dated May 19, 2000.
International Search Report for International Application No. PCT/JP00/08558 dated Jan. 4, 2002.
International Search Report for International Application No. PCT/US02/17144 dated Aug. 22, 2002.
Jin et al., "A new route to water soluble porphyrins: phosphonium and ammonium type cationic porphyrins and self-assembly", Chem. Commun., pp. 1939-1940 (1996).
Joester et al., "Superoxide Dismutase Activity of Cu2+-Amino Acid Chelates", FEBS Letters 25(1):25-28 (1972).
Kariya et al., "Superoxide Dismutase (SOD) Activity with Fe-chlorin e6-Na and Suppression of Malignant Tumor Growth in Rats", Cancer Biotheraphy 10(2):139-145 (1995).
Kaufmann et al., "Separation of the Rotational Isomers of Tetrakis(N-methyl-2-pyridiniumyl)porphyrin and Crystal Structure of a,a,a,R-(Tetrakis(N-methyl-2-pyridiniumyl)porphyrin)copper Hexacyanoferrate", Inorg. Chem. 34:5073-5079 (1995).
Keinan et al., "Catalytic Antibodies. Circular Dichroism and UV-Vis Studies of Antibody-Metalloporphyrin Interactions", Inorg. Chem. 31:5433-5438 (1992).
Kobayashi et al, "Oxidative Stress Relief for Cancer-Bearing Hosts by the Protein-Bound Polysaccharide of Coriolus versicolor QUEL with SOD Mimicking Activity", Cancer Biotherapy 9(1):55-62 (1994).
Koerner "Carbon monoxide production during the oxygenation of cobalt complexes of linear etrapyrroles", Inorg. Chem. 37(5):982-988 (1998).
Konorev et ai, "Cell-Permeable Superoxide Dismutase and Glutathione Peroxidase Mimetics Afford Superior Protection against Doxorubicin-Induced Cardiotoxicity: The Role of Reactive Oxygen and Nitrogen Intermediates", Archives of Biochemistry and Biophysics 368(2):421-428 (1999).
Kumar et al., "Radioprotection by Antioxidant Enzymes and Enzyme Mimetics", Pharmac. Ther. 39:301-309 (1988).
Laehdesmaeki et al, "Detection of Oxygen Consumption of Cultured Adherent Cells by Bead Injection Spectroscopy", Analytical Chemistry 71(22):5248-5252 (1999).
Lappin, "Part III Bioinorganic Studies", Inorganic Reaction Mechanisms 7:334-343 (1981).
Lee and Smith, "Syntheses of symmetrically substituted 5-alkyl- and 5-aryl-dihydrodipyrrins and of porphyrins and bisporphyrins therefrom", J. Chem. Soc. Perkin Trans 1:1215-1227 (1997).
Lee et al., "Rapid decomposition of peroxynitrite by manganese porphyrin-antioxidant redox couples", Bioorganic & Medical Chemistry Letters 7(22):2913-2918 (1997).
Leonidas et al., "5,10,15,20-Tetrakis( , , , - -(N-tert-butyl-carbamoyl)phenyl)porphyrin: Syntheses and Redox Properties of Zinc(II) and Copper(II) Complexes", J. Org. Chem. 54:6135-6138 (1989).
Libby et al., "Cationic Porphyrin Derivatives as Inhibitors of Polyamine Catabolism", Biochemical Pharmacology 50 (9):1527-1530 (1995).
Lindsey et al, "Rothemund and Adler-Longo Reactions Revisited: Synthesis of Tetraphenylphorins under Equilibrium Conditions", J. Org. Chem. 52:827-836 (1987).
Lindsey et al, "Synthesis of tetraphenylporphyrins under very mild conditions", Tetrahedron Letters 27(41):4969-4970 (1986).
Lindsey et al, i262Cf Plasma Desorption Mass Spectrometry in the Synthesis of Porphyrin Model Systems, Anal. Chem. 64(22):2804-2814 (1992).
Liochev et al., A Cationic Manganic Porphyrin Inhibits Uptake of Paraquat by Escherichia coil, Archives of Biochemistry and Biophysics 321(1):271-275 (1995).
Longo et al., "The Synthesis and Som e Physical Properties of ms-Tetra(pentafluorophenyl)-porphin and msTetraphenylporphines (1)", Notes 6:927-931 (1969).
Lord, "Redox characteristics of nickel and palladium complexes of the open-chain tetrapyrrole octaethylbilindione: a biliverdin model", Inorg. Chem. 39(6):1128-34 (2000).

Louati et al., "Homophophyrines: Effets D'Une Coupure De Conjugaison Cyclique Sur La Reactivite Redox Des Porphyrines", Nouv. J. Chim. 2:163-168 (1978).
Lowe et al., "Comparison of the cardiovascular effects of two novel superoxide dismutase mimetics, SC-55858 and SC-54417, in conscious dogs", European Journal of Pharmacoloty 304:81-86 (1996).
Mabley et al, "Part II: Beneficial Effects of the Peroxynitrite Decomposition Catalyst FP15 in Murine Models of Arthritis and Colitis", Molecular Medicine 8(10):581-590 (2002).
Mackensen et al., "Neuroprotection from Delayed Postischemic Administration of a Metalloporphyrin Catalytic Antioxidant", The Journal of Neuroscience 21(13):4582-4592 (2001).
Madakyan et al., "New watersoluble metal complexes of meso-tetrakis[3-N-(2'-hydroxyethyl)pyridyl]porphyrins and their pharmacological activity", Arm., Khim. Zh. 42(11):724-728-Chemical Abstracts 113:653—Abstract No. 114907h, 1972.
Madakyan et al., "Some metal complexes of meso-tetrakis (3-N-substituted pyridyl) porphyrins and their bioactivity", Arm. Khim. Zh. 42(10):642-646 (1989).
Malinski et al., "Characterization of Conductive Polymeric Nickel(II) Tetrakis(3-methoxy-4-hydroxyphenyl)Porphyrin as an Anodic Material for Electrocatalysis", J. Electrochem. Soc. 138(7):2008-2015 (1991).
Marx, "Role of Gene Defect in Heredity ALS Clarified", Science 261:986 (1993).
McClune et al., "Catalysis of Superoxide Dismutation by Iron-Ethylenediaminetetraacetic Acid Complexes. Mechanism of the Reaction and Evidence for the Direct Formation of an Iron(III)-Ethylenediaminetetraacetic Acid Peroxo Complex from the Reaction of Superoxide with Iron(II)-Ethylenediaminetetraacetic Acid", Communications to the Editor, p. 5220-2 (1977).
McCord et al., "Superoxide Dismutase—An Enzymic Function for Erythrocuprein", Biochemistry 492, p. 346.
McCord et al., Superoxide Dismutase an Enzymic Function for Erythrocuprein (Hemocuprein), The Journal of Biological Chemistry 244(22):6049-6055 (1969).
Milgrom et al., "Redox Behaviour of Phenolic Porphyrins in Basic Solutions: A Reappraisal", Free Rad. Res. 24 (1):19-29 (1996).
Milgrom, Facile Aerial Oxidation of a Porphyrin. Part 3. "Some Metal Complexes of meso-Tetrakis-(3,5-di-tbutyl-4-hydroxyphenyl)porphyrin", J. Chem. Soc. Perkin Trans. 11:71-79 (1988).
Moisy et al., "Catalytic Oxidation of 2,6-Di-Terbutylphenol by Molecular Oxygen Electroassisted by Poly(Pyrrole Manganese-Porphyrin)", New J. Chem. 13:511-514 (1989).
Naruta et al., "High Oxygen-Evolving Activity of Rigidly Linked Manganese (III) Porphyrin Dimers. A Functional Model of Manganese Catalase", J. Am. Chem. Soc. 113:3595-3596 (1991).
Oberley et al., "Anticancer activity of metal compounds with superoxide dismutase activity", Agents and Actions 15 (5/6):535-538 (1984).
Obst et al, "Helicobacter pylori causes DNA damage in gastric epithelial cells", Carcinogenesis 21(6):1111-1115 (2000).
O'Hara et al., "Potentiation of radiation-induced cell kill by synthetic metalloporphyrins", Int. J. Radiat. Oncol. Biol. Phys. 16(4):1049-1052 (1989).
Ohkawa et al., "Assay for Lipid Peroxides in Animal Tissues by Thiobarbituric Acid Reaction", Analytical Biochemistry 95:351 (1979).
Oury et al., "Cold-induced Brain Edema in Mice", The Journal of Biological Chemistry 268(21):15394-15398 (1993).
Oury et al., "Establishment of Transgenic Mice Expressing Human Extracellular Superoxide Dismutase", American Review of Respiratory Disease 143(4):A515 (1991), International Conference Supplement Abstracts—No. 236.
Oury et al., "Immunocytochemical Localization of Extracellular Superoxide Dismutase in Human Lung", American Revew of Respiratory Disease 147(4):A713 (1993), International Conference Supplement Abstracts—No. 246.
Oury et al., "Transgenic Mice Superexpressing Human Extracellular Superoxide Dismutase Show Increased Resistance to Cold-induced Brain Edema, but are More Susceptible to Hyperbaric Oxygen", American Review of Respiratory Disease 145(4):A713, 1987.

Oury, Tim D., "Extracellular Superoxide Dismutase and Nitric Oxide: Transgenic and Immunocytochemical Studies", Dissertation submitted in partial fulfillment of the requirements for the degree of Doctor of Philosophy in the Department of Pathology in the, 1994.
Oury. et al., "Extracellular superoxide dismutase, nitric oxide, and central nervous system 02 toxicity", Proc. Natl. Acad. Sci. USA 89:9715-9719 (1992).
Parge et al., "Atomic structures of wild-type and thermostable mutant recombinant human Cu,Zn superoxide dismutase", Proc. Natl. Acad. Sci. USA 89:6109-6113 (1992).
Pasternack et al., "Aggregation of Nickel(II), Copper (II), and Zinc(II) Derivatives of Water-Soluble Porphyrins", Inorganic Chemistry 12(11):2606-2610 (1973).
Pasternack et al., "Catalyst of the Disproportionation of Superoxide by Metalloporphyrins III", Journal of Inorganic Biochemistry 15:261-267 (1981).
Pasternack et al., "Catalyst of the Disproportionation of Superoxide by Metalloporphyrins", Journal of Inorganic Biochemistry 11:261-267 (1979).
Pasternack et al., "On the Aggregation of Meso-Substituted Water-Soluble Porphyrins", Journal of American Chemical Society 94(13):4511-4517 (1972).
Pasternack et al., "Superoxide Dismutase Activities of an Iron Porphyrin and Other Iron Complexes", Journal of the American Chemical Society 101(4):1026-1031 (1979).
Patel and Day, "Metalloporphyrin class of therapeutic catalytic antioxidants", TIPS Elsevier Trends Journal 20(9):359-364(1999).
Patel et al., "Requirement for Superoxide in Excitotoxic Cell Death", Neuron 16:345-355 (1996).
Peretz et al., "Chemical properties of water-soluble porphyrins 3. The reaction of superoxide radicals with some metalloporphyrins", Int. J. Radiat. Biol. 42(4):449-456 (1982).
Picker et al., "Cobalt(III) complexes of water soluble synthetic meso-substituted porphyrins as radiation sensitizers for oxic and hypoxic tumor cells", 8-Radiation 112:405 (1990) Abstract No. 112:73026d.
Pitie et al., "Oxidation at Carbon-1' of DNA Deoxyriboses by the Mn-TMPyP/KHSO5 System Results from a Cytochrome P-450-Type Hydroxylation Reaction", J. Am. Chem. Soc. 117:2935-2936 (1995).
Poison et al, "The Effect of Liver Transplantation in a 13-Year-Old Boy with Erythropoietic Protoporphyria", Transplantation 46(3):386-389 (1988).
Registry Copyright 2004 ACS on STN, Registry No. 138025-71-5, Entered STN: Dec. 21, 1991.
Richards et al, "Observation of a Stable Water-Soluble Lithium Porphyrin", Inorg. Chem. 35:1940-1944 (1996).
Robertson, Jr. et al, "Does Copper-D-Penicillamine Catalyze the Disutatio of O2-?", Archives of Biochemistry and Biophysics 203(2) 830-831 (1980).
Rosenfeld et al., "Safety and pharmacokinetics of recombinant human superoxide dismutase administered intratracheally to premature neonates with respiratory distress syndrome", Pediatrics 97(Pt 1):811-817 (1996).
Ruoslahti et al., "Arg-Gly-Asp: A Versatile Cell Recognition Signal", Cell 44:517-518 (1986).
Sari et al., "Interaction of Cationic Porphyrins with DNA: Importance of the Number and Position of the Charges and Minimum Structural Requirements for Intercalation", Biochemistry 29:4205-4215 (1990).
Schlozer et al., "Reactivity of Unsubstituted Porphin", German version: Angew. Chem. 87:388 (1975).
Schneider et al., "Ligand-Porphyrin Complexes: Quantitative Evaluation of Stacking and Ionic Contributions", J. Org. Chem. 59:7464-7472 (1994).
Sharma et al., "Synthesis of amphiphilic 5-(4-N-alkylpyridiniumyl)-10,15,20-triphenylporphyrins and their aggregational properties in different solvent systems", Chemical Abstracts vol. 123, No. 1 (1995)—Abstract No. 9222q.
Sheldon, Chapter 1 in Metalloporphyrins in Catalytic Oxidations, Marcel Dekker, Inc. (1994).
Shimanovich et al, "Mn(II)-Texaphyrin as a Catalyst for the Decomposition of Peroxynitrite", J. Am. Chem. Soc. 123:3613-3614 (2001).
Solomon et al., "Chemical properties of Water-Soluble Porphyrins. 2. The Reaction of Iron(III) Tetrakis(4 Nmethylpyridyl)porphyrin with the Superoxide Radical Dioxygen Couple", J. Phys. Chem. 86:1842-1849 (1982).
Song et al., "Anti-HIV activities of anionic metalloporphyrins and related compounds", Antiviral Chemistry and Chemotherapy 8(2):85 (1997).
Sonis et al, "AEOL 10150, a catalytic antioxidant, reduces the incidence and duration of radiation-induced oral mucositis in a hamster", European Journal of Cancer 37:S361 (2001)—Abstract.
Sorenson, John R.J., "Copper Chelates as Possible Active Forms of the Antiarthritic Agents", Journal of Medicinal Chemistry 19(1):135-148 (1976).
Spasojevic et al., "Manganese(III) complexes with porphyrins and related compounds as catalytic scavengers of superoxide", Inorganica Chimica Acta 317:230-242 (2001).
Stralin et al., "Effects of Oxidative Stress on Expression of Extracellular Superoxide Dismutase, CuZnSuperoxide Fibroblast", Biochem. J. 298:347-352 (1994).
Supplementary European Search Report for EP02739551 dated Aug. 5, 2009, 4 pages.
Szabo et al, "Part I: Pathogenetic Role of Peroxynitrite in the Development of Diabetes and Diabetic Vascular Complications: Studies With FP15, a Novel Potent Peroxynitrite Decomposition Catalyst" Molecular Medicine 8(10):571-580 (2002).
Szabo et al., "Evaluation of the relative contribution of nitric oxide and peroxynitrite to the suppression of mitochondrial respiration in immunostimulated macrophages using a manganese mesoporphyrin superoxide dismutase mimetic and peroxynitrite scavenger", 1999.
Szabo et al., "Peroxynitrite is Involved in the Pathogenesis of the Vascular Contractile and Energetic Failure in Endotoxic Shock", Shock Society Meeting (1996).
Tjahjono et al., "Cationic porphyrins . . . ", Biochmica et Biophysica Acta 1472 (1999) 333-343. Note: Closest prior art.
Tsan, M-F., "Superoxide Dismutase and Pulmonary Oxygen Toxicity," XP-002074505, pp. 286-290, 1994.
Tsvetkov et al, "Infrared spectra of copper complexes of tetraphenylporphyrin", Izvestiya Vrvysshikh Uchebnykh Zavedenij, Khimiya I Khimicheskaya Tekhnologiya 27(7):782-785 (1984)—English Abstract.
Vergeldt et al., "Intramolecular Interactions in the Ground and Excited State of Tetrakis(N-methylpyridyi) porphyrins", J. Phys. Chem. 99:4397-4405 (1995).
Vinogradov and Wilson, "Palladium catalyzed carbonylation of Br-substituted porphyrins", Tetrahedron Letters 39(49):8935-8938 (1998).
Vodzinskii et al., "Porphyrines and Their Derivatives. XX. Synthesis and Properties of 2-Nitro-5,10,15,20 tetraheterylporphyrins", Russian Journal of Organic Chemistry 34(6):882-885 (1998).
Walker et al, "Models of the cytochromes b, 5. EPR Studies of low-spin iron(III) tetraphenylporphyrins", Journal of the American Chemical Society 106(23):6888-6898 1984).
Wang et al, Structure of LB film of 5,10,15,20-tetra(p-ethoyycarbonphenyl)porphyrin, Yingyong Huaxue 10(21:87-88 (1993)—English Abstract.
Weinraub et al., "Chemical Properties of Water-Soluble Porphyrins. 1. Equilibria between Some Ligands and Iron (III) Tetrakis (4-N-methylpyridyl)porphyrin", J. Phys. Chem. 86:1839-1842 (1982).
Weinraub et al., "Chemical properties of water-soluble porphyrins. 5. Reactions of some manganese (III) porphyrins with the superoxide and other reducing radicals", Int. J. Radiat. Biol. 50(4):649-658 (1986) (Abs).
Weiss et al., "Evaluation of Activity of Putative Superoxide Dismutase Mimics", The Journal of Biological Chemistry 268(31):23049-23054 (1993).
Weiss et al., "Manganese-based Superoxide Dismutase Mimetics Inhibit Neutral Infiltration in Vivo", The Journal of Biological Chemistry 271(42):26149-26156 (1996).
Werringloer et al., "The Interaction of Divalent Copper and the Microsomal Electron Transport System", The Journal of Biological Chemistry, 254(23):11839-11846 (1979).

Wheelhouse et al., "Cationic Porphyrins as Telomerase Inhibitors; the Interaction of Tetra-(N-methyl-4pyridyl) porphine with Quadruplex DNA", J. Am. Chem. Soc. 120(13):3261-3262 (1998).

White et al, "A Highly Stereoselective Synthesis of Epothilone B", J. Org. Chem. 64:684-685 (1999).

Winkelman, James, "The Distribution of Tetraphenylporphinesulfonate in the Tumor-bearing Rat", Cancer Research 22:589-596 (1962).

Wolberg et al., "Electrocical and electron paramagnetic resonance studies of metalloporphyrins and their electrochemical oxidation products", Journal of the American 92(10):2982-90 (1970).

Yu and Su, "Electrocatalytic reduction of nitric oxide by water-soluble manganese porphyrins", Journal of Electroanalytical Chemistry 368:323-327 (1994).

Yue et al., "Carvedilol, a New Vasodilator and Beta Adrenoceptor Antagonist, is an Antioxidant and Free Radical Scavenger", The Journal of Phramacology and Experimental Therapeutics 263:(1992).

Zahedi, "Semiempirical molecular orbital calculations of biliverdin: study of dynamics and energetics of the self association of a two-electron oxidation product", Theochem. 531:79-88 (2000).

Canti, G. et al., "Hematoporphyrin derivative rescue from toxicity caused by chemotherapy or radiation in a murine leukemia model (L1210)", Cancer Research 44:1551-1556, Apr. 1984.

European Search Report for European Application No. EP09805313.5 dated Mar. 1, 2012, 14 pages.

McClintock, Shannon D. et al., "Attenuation of half sulfur mustard gas-induced acute lung injury in rats", Journal of Applied Toxicology 26:126-131, 2006.

O'Neill, Heidi C. et al., "Catalytic antioxidant AEOL 10150 ameliorates 2-chloroethyl ethyl sulfide (CEES)-induced lung injury in rats", Free Radical Biology & Medicine 45(1):S89, 2008.

Gould, Neal S. et al., "A role for mitochondrial oxidative stress in sulfur mustard analog 2-chloroethyl ethyl sulfide-induced lung cell injury and atioxidant protection", The Journal of Pharmacology and Experimental Therapeutics 328(3):732-739, Mar. 2009.

* cited by examiner

HBSS Control

SOD mimic

SOD mimic

SOD mimic

AEOL-10112

Aeol-10113

Aeol-10150

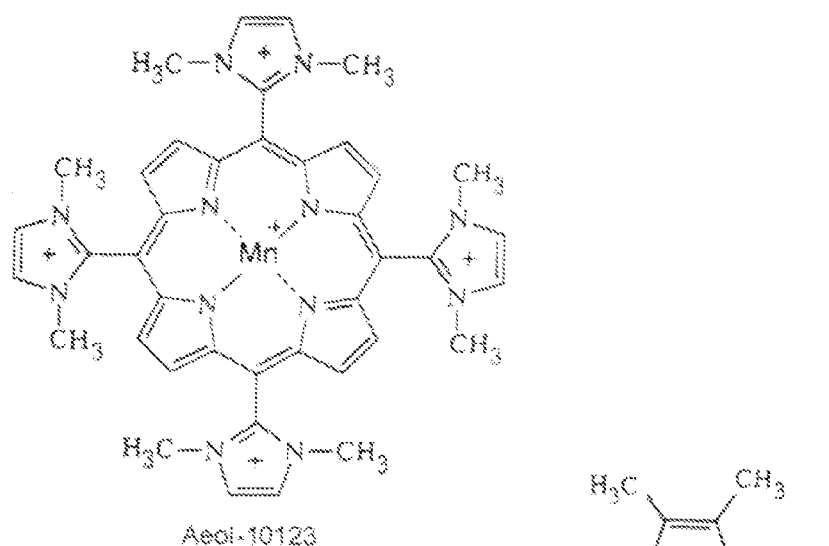
Figure 9D
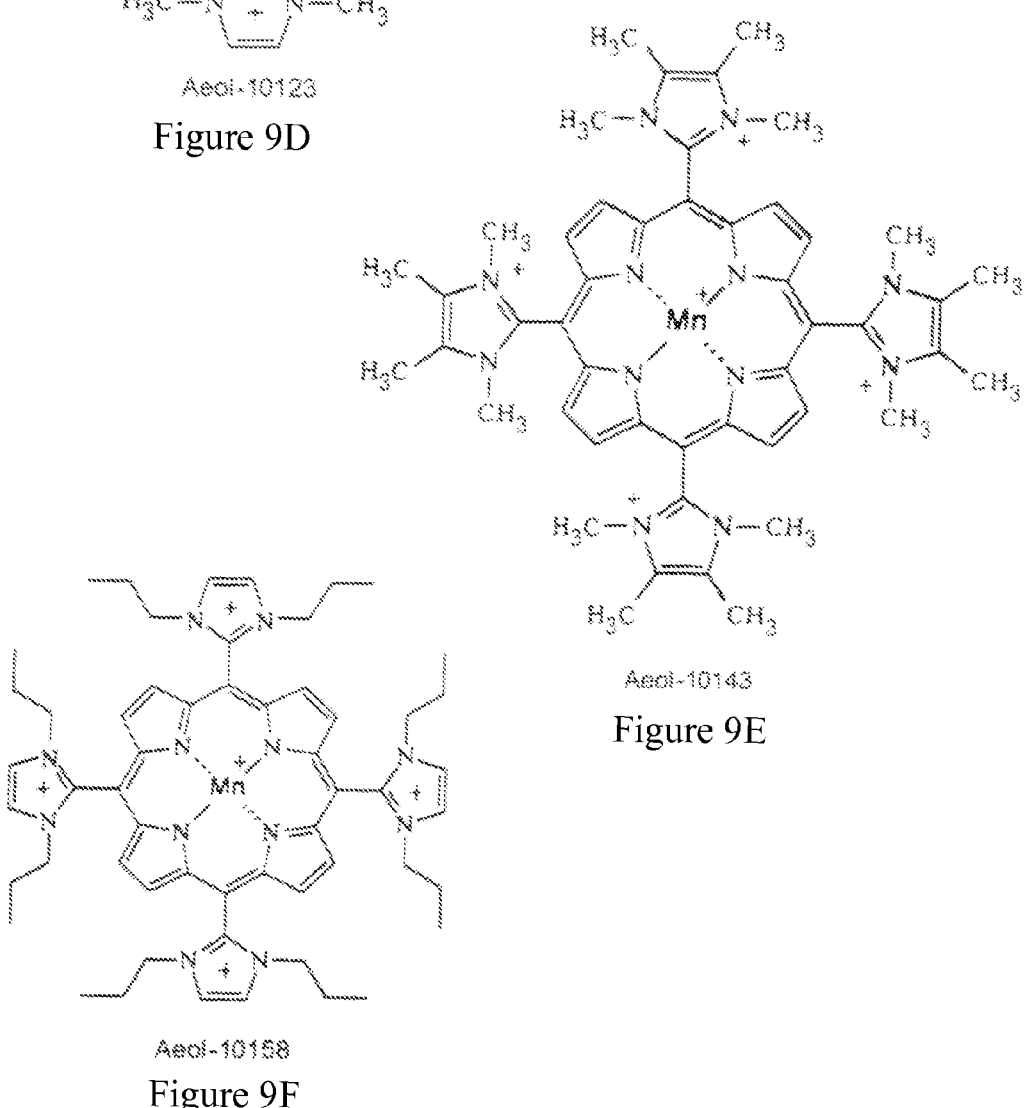
Figure 9E
Figure 9F

| Donor Tissue Exp. Groups | Pro-Insulin | Glucagon | Amylase | CK19 | Time of Evaluation |
|---|---|---|---|---|---|
| HP49 | 43 | 15 | 25* | 20 | at start |
| Control | 50 | 21 | 5 | 14 | after culture |
| SOD | 55 | 11 | 5 | 12 | |
| HP50 | 43 | 15 | 20* | 10 | at start |
| Control | 40 | 12 | 9 | 12 | after culture |
| SOD | 46 | 17 | 3 | 12 | |
| HP53 | 45 | 6 | 25* | 15 | at start |
| Control | 50 | 5 | <5 | 12 | after culture |
| SOD | 65 | 5 | 5 | 20 | |
| HP54 | 55 | 10 | 10* | 20 | at start |
| Control | 35 | 15 | 0 | 20 | after culture |
| SOD | 40 | 17 | 0 | 22 | |
| HP55 | 35 | 12 | 30* | 18 | at start |
| Control | 47 | 25 | 0 | 22 | after culture |
| SOD | 46 | 24 | 0 | 20 | |

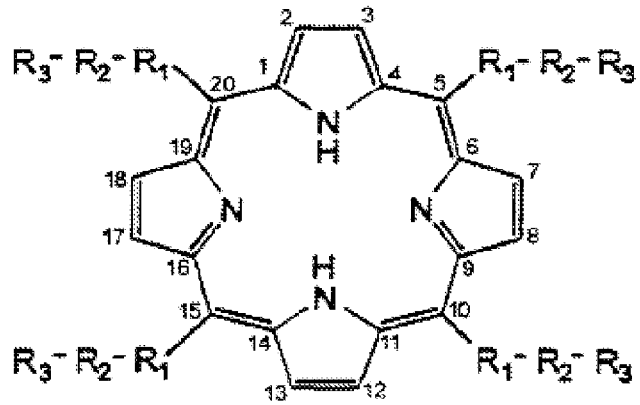

or a pharmaceutically acceptable salt thereof, wherein:

$R_1$ is a bond, –⌬H, –⌬, –⌬N⁺, –⌬NO₂, –⌬SO₃H, –⌬SO₃⁻, –⌬X, or –⌬Y wherein X is a halogen and Y is an alkyl group and wherein ⌬ indicates bonding to $R_2$ at any position and ⌬ indicates bonding to $R_2$ and the substituent at any position; and $R_2$ is a bond, $-(CY'_2)_n-$, $-(CY'_2-CY'=CY')_n-$, $-(CY'_2-CY'_2-CH=CH)_n-$, $-(CY'=CY')_n-$, or $-(CY'_2-\overset{O}{\underset{\|}{C}})_n-$, wherein Y' is hydrogen or an alkyl group and wherein n is 1 to 8; and $R_3$ is $-Y''$, $-OH$, $-NH_2$, $-N^+(Y'')_3$, $-COOH$, $-COO^-$, $-SO_3H$, $-SO_3^-$, $-C-PO_3H_2$ or $-C-PO_3H^-$, wherein Y'' is an alkyl group.

Figure 18A

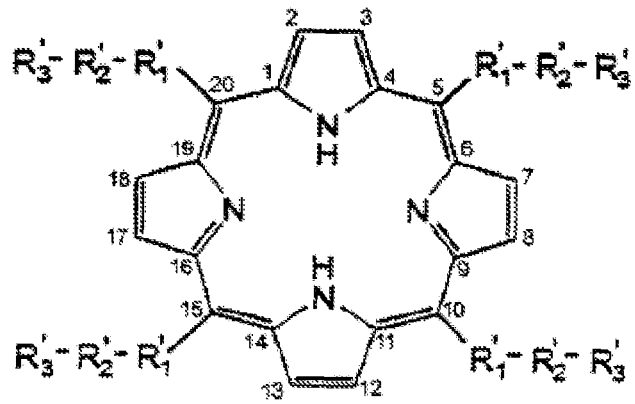

or a pharmaceutically acceptable salt thereof, wherein:

each $R_1'$ is independently a bond, ⌬-$CO_2Y''$, ⌬-$OH$, ⌬, ⌬-$Y''$, ⌬-$CO_2H$, ⌬-$\overset{O}{\overset{\|}{C}}$-NH-, ⌬-$\overset{O}{\overset{\|}{C}}$-$\overset{O}{\overset{\|}{C}}$-, ⌬-$\overset{O}{\overset{\|}{C}}$-, or ⌬-$\overset{CY''_3}{\underset{CY''_3}{C}}$, wherein $Y''$ is an alkyl group, and wherein ⌬ indicates bonding to $R_2'$ at any position and ⌬ indicates bonding to $R_2'$ and the $R_1'$ phenyl substituent at any position;

each $R_2'$ is independently a bond, or -$(CH_2)_n$- wherein n is 1-4, each $R_3'$ is independently -$Y''$, -$Y'''$, -H, -OH, -$OY''$, -$NO_2$, -CN, -$NH_2$, -COOH, -$COY''$, -$COO^-$, or a heterocyclic group, wherein $Y''$ is as defined above and $Y'''$ is a primary, secondary, tertiary or quaternary amine.

Figure 18B

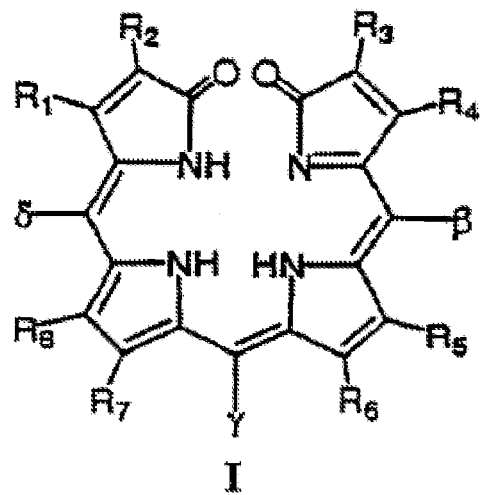

I

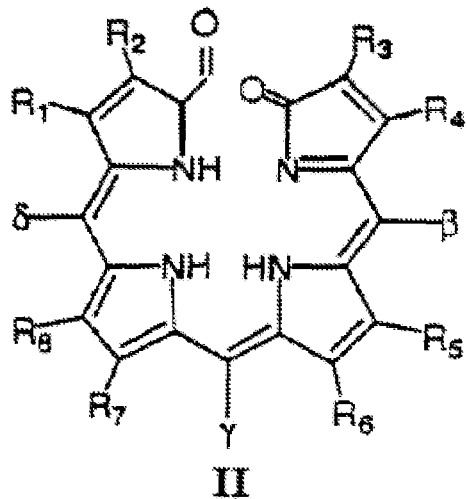

II $R_1$ through $R_8$ are, independently, -H, alkyl, 2-hydroxyalkyl, methoxyalkyl, halogen, nitro, cyano, trialkylammonium, formyl, amide of carboxylic acid, alkyl ester of carboxylic acid, carboxylic acid, glucuronyl or glyceryl ester of carboxylic acid, 1,2-dihydroxyalkyl, acetyl, vinyl, glycosyl or, taurate, and $\beta$, $\gamma$ and $\delta$ are, independently, -H, acetyl, glycyl, benzoate, phenylsulfonate, 2-, or 3-, or 4-N-alkyl-pyridyl, nitrophenyl, halophenyl, methoxyalkyl, halogen, nitro, cyano, trialkylammonium, formyl, amide of carboxylic acid.

Figure 18C or a pharmaceutically acceptable salt thereof, wherein:

$R_1$ and $R_3$ are the same and are:

$R_2$ and $R_4$ are the same and are:

Y is halogen or $-CO_2X$,
each X is the same or different and is an alkyl and
each $R_5$ is the same or different (preferably the same) and is H or alkyl.

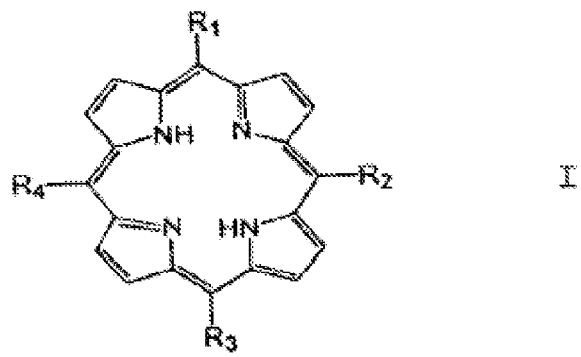

or pharmaceutically acceptable salt thereof
wherein:

$R_1$ and $R_3$ are, independently:

-$CO_2C_{1-4}$alkyl; or

-$CO_2(CH_2)_nCX_3$, wherein X is halogen and n = 1 to 3;

$R_2$ is:

-H

-$C_{1-4}$alkyl

-COOH

-$CO_2C_{1-4}$alkyl,

-$CO_2(CH_2)_nCX_3$, wherein X is halogen and n = 1 to 3,

-$CON(CH_3)_2$, or

-$CX_3$, wherein X is halogen; and $R_4$ is:

-H,

-$C_{1-4}$alkyl

-COOH,

-$CO_2C_{1-4}$alkyl,

-$CO_2(CH_2)_nCX_3$, wherein X is halogen and n = 1 to 3,

-$CON(CH_3)_2$, or

-$CX_3$, wherein X is halogen.

Figure 18F

I or II, or pharmaceutically acceptable salt thereof, wherein each R is, independently, a $C_1$-$C_8$ alkyl group, and each P is, independently, an electron withdrawing group or hydrogen.

Catalytic Antioxidant Metalloporphyrin
[MnTBAP]

OXIDANT SCAVENGERS FOR TREATMENT OF TYPE I DIABETES OR TYPE II DIABETES

CROSS-REFERENCES TO RELATED APPLICATIONS

This application is a continuation of U.S. application Ser. No. 11/857,949, filed Sep. 19, 2007, which in turn is a continuation of U.S. application Ser. No. 10/159,280, filed Jun. 3, 2002, which is a non provisional of U.S. Provisional Application Nos. 60/328,398, filed Oct. 12, 2001, and 60/294,604, filed Jun. 1, 2001; and a continuation-in-part of U.S. application Ser. No. 11/424,662, filed Jun. 16, 2006, which is a divisional of U.S. application Ser. No. 10/349,171, filed Jan. 23, 2003 (now U.S. Pat. No. 7,189,707 issued Mar. 13, 2007), which is a continuation of U.S. application Ser. No. 09/490,537, filed Jan. 25, 2000 (now U.S. Pat. No. 6,544,975 issued Apr. 8, 2003), which is a non provisional of U.S. Provisional Application No. 60/117,010, filed Jan. 25, 1999.

TECHNICAL FIELD

The present invention relates, in one embodiment, to a method of preventing or treating diabetes using low molecular weight antioxidants. In a further embodiment, the invention relates to a method of protecting and/or enhancing viability of cells/tissues/organs during isolation (harvesting), preservation, expansion and/or transplantation. In yet another embodiment, the present invention relates to a method of inducing immune tolerance. The invention also relates to compounds and compositions suitable for use in such methods.

BACKGROUND OF THE INVENTION

Diabetes is characterized by chronic hyperglycemia. There are 2 forms of the disease, insulin dependent (Type I) and non-insulin dependent (Type II). The disease process associated with both Type I and Type II includes a microvascular pathology that can result, for example, in blindness, renal failure and nerve damage. In addition, an accelerated atherosclerotic macrovascular pathology can affect arteries supplying the heart, brain and lower extremities. (See, for example, Brownlee, Nature 414:813 (2001).)

Type I diabetes is caused by the autoimmune destruction of insulin-producing pancreatic β cells. A large body of evidence supports the concept that the antigen-specific, T cell-mediated infiltration of inflammatory cells to the pancreas leads to the generation of reactive oxygen species (ROS) [superoxide, ($O_2^-$), hydroxyl radical (.OH), nitric oxide (NO.), peroxynitrite ($ONOO^-$)], and pro-inflammatory cytokines (TNF-α, IL-1β (interleukin 1β) and IFN-γ (interferon γ) (Rabinovitch et al, Endocrinology 137:2093-2099 (1996), Mandrup-Poulsen, Diabetologia 39:1005-1029 (1996), Eizirik et al, Diabetologia 39:875-890 (1996), Mandrup-Poulsen et al, Eur. J. Endocrinol. 134:21-30 (1996)). Synergistic interaction between ROS (reactive oxygen species) and these cytokines results in the ultimate destruction of the pancreatic β cells.

Locally produced ROS are involved in the effector mechanisms of β cell destruction (Rabinovitch et al, Endocrinology 137:2093-2099 (1996), Mandrup-Poulsen, Diabetologia 39:1005-1029 (1996), Eizirik et al, Diabetologia 39:875-890 (1996), Grankvist et al, Biochem. J. 182:17-25 (1979), Kroncke et al, Biochem. Biophys. Res. Commun. 175:752-758 (1991), Corbet et al, J. Clin. Invest. 90:2384-2391 (1992)). In vitro, T cell and macrophage cytokines such as IFN-γ, IL-1β and TNF-α (tumor necrosis factor-α) induce the production of ROS by β cells. In addition, ROS either given exogenously or elicited in β cells by cytokines lead to β cell destruction (Lortz et al, Diabetes 49:1123-1130 (2000)). This destruction appears to ultimately be caused by an apoptotic mechanism (Kurrer et al, Proc. Natl. Acad. Sci. USA 94:213-218 (1993), O'Brien et al, Diabetes 46:750-757 (1997), Chervonski et al, Cell 89:17-24 (1997), Itoh et al, J. Exp. Med. 186:613-618 (1997)). β cells engineered to over-express antioxidant proteins have been shown to be resistant to ROS and NO. (Grankvist et al, Biochem. J. 199:393-398 (1981), Malaisse et al, Proc. Natl. Acad. Sci. USA 79:927-930 (1982), Lenzen et al, Free Radic. Biol. Med. 20:463-465 (1996), Tiedge et al, Diabetes 46:1733-1742 (1997), Benhamou et al, Diabetologia 41:1093-1100 (1998), Tiedge et al, Diabetes 47:1578-1585 (1998), Tiedge et al, Diabetologia 42:849-855 (1999)). Furthermore, stable expression of manganese superoxide dismutase (Mn-SOD) in insulinoma cells prevented IL-1β-induced cytotoxicity and reduced nitric oxide production (Hohmeier et al, J. Clin. Invest. 101:1811-1820 (1998)). Finally, others have shown that transgenic mice with β cell-targeted over-expression of copper, zinc SOD or thioredoxin are resistant to autoimmune and streptozotocin-induced diabetes (Kubisch et al, Proc. Natl. Acad. Sci. USA 91:9956-9959 (1994), Kubisch et al, Diabetes 46:1563-1566 (1997), Hotta et al, J. Exp. Med. 188:1445-1451 (1998)).

SOD mimics have been designed with a redox-active metal center that catalyzes the dismutation of $O_2^-$ in a manner similar to the active metal sites of the mammalian Cu, Zn- or Mn-containing SODs (Fridovich, J. Biol. Chem. 264:7761-7764 (1989), Pasternack et al, J. Inorg. Biochem. 15:261 (1981), Faulkner et al, J. Biol. Chem. 269:23471-23476 (1994), Batinic-Haberle et al, J. Biol. Chem. 273:24521-24528 (1998), Patel et al, Trends Pharmacol. Sci. 20:359-364 (1999), Spasojevic et al, Inorg. Chem. 40:726 (2001)). The manganese porphyrins have a broad antioxidant specificity, which includes scavenging $O_2^-$ (Batinic-Haberle et al, Inorg. Chem. 38:4011 (1999)), $H_2O_2$ (Spasojevic et al, Inorg. Chem. 40:726 (2001), Day et al, Arch. Biochem. Biophys 347:256-262 (1997)), $ONOO^-$, (Ferrer-Sueta et al, Chem. Res. Toxicol. 12:442-449 (1999)), $NO^-$ (Spasojevic et al, Nitric Oxide: Biology and Chemistry 4:526 (2000)) and lipid peroxyl radicals (Day et al, Free Radic. Biol. Med. 26:730-736 (1999)). SOD mimics have recently been found to rescue vascular contractility in endotoxic shock (Zingarelli et al, Br. J. Pharmacol. 120:259-267 (1997)), protect neuronal cells from excitotoxic cell death (Patel et al, Neuron 16:345-355 (1996)) and apoptosis (Patel, J. Neurochem. 71:1068-1074 (1998)), inhibit lipid-peroxidation (Day et al, Free Radic. Biol. Med. 26:730-736 (1999), Bloodsworth et al, Free Radic. Biol. Med. 28:1017-1029 (2000)), block hydrogen peroxide-induced mitochondria) DNA damage (Milano et al, Nucleic Acids Res. 28:968-973 (2000)), and partially rescue a lethal phenotype in a manganese superoxide dismutase knockout mouse (Melov et al, Nat. Genet. 18:159-163 (1998)). The ability of the SOD mimics to scavenge a broad range of ROS allows for their utilization in inflammatory diseases.

The present invention provides a pharmacological approach to protect β cells from the T cell mediated ROS and cytokine destruction associated with autoimmune diabetes by employing a synthetic metalloporphyrin-based superoxide dismutase mimic. The invention also provides a method of improving survival of pancreatic β islet cells following transplantation.

BRIEF SUMMARY OF THE INVENTION

The present invention relates, in one embodiment, to a method of preventing or treating diabetes using low molecular weight antioxidants. In accordance with this embodiment, low molecular weight antioxidants can be used to treat or prevent diabetes-specific microvascular disease of, for example, the retina, renal glomerulus and peripheral nerve (e.g., resulting in oedema, ischaemia and hypoxia-induced neovascularization in the retina, proteinuria, mesangial matrix expansion and glomerulosclerosis in the kidney, and multifocal axonal degeneration in peripheral nerves). In addition, low molecular weight antioxidants can be used to treat or prevent accelerated atherosclerotic macrovascular disease affecting arteries supplying the heart, brain and lower extremities. In a further embodiment, the invention relates to a method of protecting and/or enhancing viability of cells/tissues/organs during isolation (harvesting), preservation, expansion and/or transplantation. In yet another embodiment, the present invention relates to a method of inducing immune tolerance. The invention also relates to compounds and compositions suitable for use in such methods.

Objects and advantages of the present invention will be clear from the description that follows.

BRIEF DESCRIPTION OF THE DRAWINGS

FIG. 1A. NOD.scid mice 9-14 days of age were injected i.p., one day prior to adoptive transfer of $1 \times 10^7$ BDC-2.5 T cell clones, with 10 mg/kg of the SOD mimic • or HBSS control ■. The SOD mimic was then given every other day for a total of 5 days. The data represented in FIG. 1A is the combination of 3 separate experiments. FIG. 1B. Representative pancreatic histology from young NOD.scid mice treated with SOD mimic or control after adoptive transfer of the T cell clone BDC-2.5. FIG. 1Ba. Hematoxylin and Eosin (H&E) staining of a heavily infiltrated pancreas from the positive control, a young NOD.scid mouse after adoptive transfer of BDC-2.5. FIG. 1Bb.,c. H & E staining of pancreas from young NOD-.scid treated with SOD mimic (10 mg/kg) after adoptive transfer of BDC-2.5. FIG. 1Bd. Aldehyde-fuchsin (A/F) staining of pancreas from SOD mimic-treated NOD.scid mouse.

FIG. 2A. 96-well round bottom plates were pre-coated with 0.125 ug/ml α-CD3 and 1 μg/ml α-CD28 for 1 hr at 37° C. The plates were washed twice with sterile HBSS and then blocked with complete medium (CM) at 37° C. for 1 hour. Blocking solution was removed and $2 \times 10^4$ BDC-2.5 T cell clones were added to the wells in the presence or absence of the SOD mimic at concentrations of 34 and 17 μM; the negative control was BDC-2.5 without α-CD3 and α-CD28. Cultures were incubated at 37° C. for 48 hr before the supernatants were harvested and assayed by sandwich ELISA for IFN-γ production. Data are the mean and SEM of 3 separate experiments; p values are shown for conditions where statistical significance was noted. FIG. 2B. BDC-2.5 T cells were plated at $2 \times 10^4$ cells/well in 96-well flat-bottom plates with or without $5 \times 10^5$ irradiated syngeneic spleen cells as APC (antigen presenting cell/s) and Con A (2.5 μg/ml final concentration), in the presence or absence of the SOD mimic at concentrations of 34 μM and 17 μM. Cultures were incubated at 37° C. for 24 hr before the supernatants were harvested and assayed by sandwich ELISA for IFN-γ production. Data are the mean and SEM of 3 separate experiments. FIG. 2C. BDC-2.5 T cell clones were cultured in 96-well flat-bottom plates at a density of $2 \times 10^4$ cells/well, with 5000 islet-cells as antigen and $2.5 \times 10^4$ APC, in the presence or absence of SOD mimic at 34 and 17 μM. Cultures were incubated at 37° C. for 48 hr before the supernatants were harvested and assayed by sandwich ELISA for IFN-γ production. Data are the mean and SEM of 3 separate experiments.

FIG. 4A. Peritoneal macrophages (PC) were harvested from unprimed NOD mice and plated ($5 \times 10^5$ cells/well) in 24-well plates in CM with *E. coli* LPS (055:B5) at 200 ng/ml in the presence or absence of the SOD mimic at 34 μM or 3.4 μM final concentration. Cultures were incubated at 37° C. for 48 hr; the cells were trypsinized, and washed to remove the trypsin, and subsequently transferred to microfuge tubes. PMA was added to a final concentration of 50 ng/ml. After incubation at 37° C. for 20 min, superoxide production was assessed spectrophotometrically by ferricytochrome c reduction using an $\epsilon = 20{,}000$ $M^{-1}$ $cm^{-1}$. The reduction was monitored over a period of 10 min. Data are mean and SEM or triplicate wells and representative of duplicate experiments. FIG. 4B. Peritoneal macrophages were harvested from unprimed NOD mice by washing the cavity of each animal with 7 ml of HBSS. The cells were then washed 2× in sterile HBSS and adjusted to $5 \times 10^5$ cells/well in a 24 well plate in CM with *E. coli* LPS (05:B5) at 200 ng/ml in the presence or absence of 34 μM or 17 μM son mimic. Cultures were incubated at 37° C. for 48 hr before the supernatants were harvested and assayed by specific sandwich ELISA for TNF-α. The data are the mean and SEM of 3 separate experiments.

FIG. 5A. NIT-1 cells were grown to confluence in 12-well tissue culture dishes. Media was removed and replaced with PBS alone or PBS containing 34 μM SOD mimic. All solutions were supplemented with 4% FCS. After 1 hour incubation, 10 mM alloxan was added to the appropriate wells, and cells were incubated for an additional 2 hours. Cells were washed, collected by trypsinization and processed for viability via ethidium bromide/acridine orange fluorescence □ live, ■ live apoptotic. Data are representative of duplicate experiments. FIG. 5B. NIT-1 cells were grown to 80% confluence in 12-well plastic tissue culture dishes. Growth media was removed and replaced with 500 μl/well of either media alone or media+34 μM SOD mimic. After 1 hour incubation, 500 μl/well of media alone, media or 20 ng/ml TL-1 (10 ng/ml final concentration)+/−34 uM SOD mimic were added. Cells were incubated an additional 48 hr, and assessed for viability via ethidium bromide/acridine orange fluorescence □ live, ■ live apoptotic. Values are the mean and SEM of triplicate wells per treatment.

FIGS. 9A-F. Structures of specific prophyrins mimetics.

FIG. 12A. Timecourse of cell death in cortical cultures from SOD2 knockout (+/+, +/− or −/−) mice after serum withdrawal in ambient oxygen levels. n=16-20, *p<0.01. FIGS. 12B and 12C. Effect of AEOL compounds to inhibit cell death 2 and 3 days after serum withdrawal in SOD2−/− cultures. n=10-16 cultures.

FIGS. 18A-K. Structures of certain generic and specific definitions of compounds suitable for use in the invention (in free or metal-bound forms). With reference to FIG. 18C, mimetics of the invention can be of Formula I or II, or dimeric forms thereof, an example being shown in FIG. 18D.

DETAILED DESCRIPTION OF THE INVENTION

The present invention relates to methods of preventing or treating diabetes using low molecular weight antioxidants (e.g., mimetics of scavengers of reactive oxygen species, including mimetics of SODS, catalases and peroxidases). In accordance with the invention, the present mimetics can be used to prevent, delay the onset of and/or limit the severity of diabetes resulting, for example, from the death of pancreatic islet cells due to autoimmune diseases or free radical induced toxicity, or toxins or drugs the effects of which are mediated by free radical damage. Low molecular weight antioxidants can be used to treat or prevent diabetes-specific microvascular disease of, for example, the retina, renal glomerulus and peripheral nerve (e.g., resulting in oedema, ischaemia and hypoxia-induced neovascularization in the retina, proteinuria, mesangial matrix expansion and glomerulosclerosis in the kidney, and multifocal axonal degeneration in peripheral nerves). In addition, low molecular weight antioxidants can be used to treat or prevent accelerated atherosclerotic macrovascular disease affecting arteries supplying the heart, brain and lower extremities.

The invention further relates to a method of enhancing cell survival (for example, (3 islet cell survival) following transplantation. The invention further relates to formulations suitable for use in such methods.

Figure 9A:
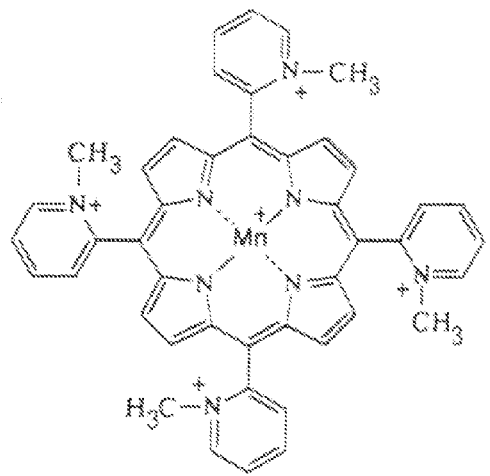
Figure 9B:
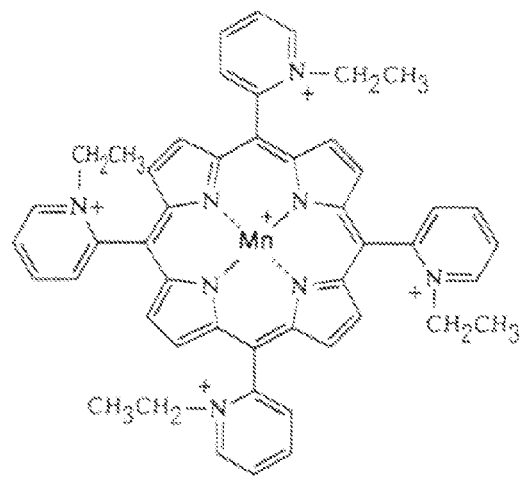
Figure 9C:
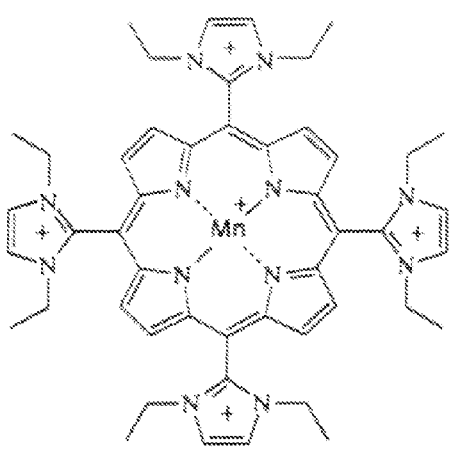

Mimetics of scavengers of reactive oxygen species appropriate for use in the present methods include methine (i.e., meso) substituted porphines and substituted tetrapyrroles, or pharmaceutically acceptable salts thereof (e.g., chloride or bromide salts). The invention includes both metal-free and metal-bound porphines and tetrapyrroles. In the case of metal-bound porphines and tetrapyrroles, manganic derivatives are preferred, however, metals other than manganese such as iron (II or III), copper (I or II), cobalt (II or III), or nickel (I or II), can also be used. It will be appreciated that the metal selected can have various valence states, for example, manganese II, III, IV or V can be used. Zinc (II) can also be used even though it does not undergo a valence change and therefore will not directly scavenge superoxide. The choice of the metal can affect selectivity of the oxygen species that is scavenged. Examples of such mimetics are shown in FIG. 9, FIG. 18 and/or are described in U.S. Pat. Nos. 5,994,339, 6,103,714 and U.S. Pat. No. 6,127,356 and in U.S. application Ser. Nos. 09/184,982, 09/296,615, 09/490,537, 09/880,075 and 60/211,857 (these applications are incorporated in their entirety by reference). Appropriate methods of synthesis are described in these patents and applications.

In addition to the mimetics described in the above-identified patents and applications, other nonproteinaceous catalytic antioxidants can also be used, including manganese salen compounds (Baudry et al, Biochem. Biophys. Res. Commun. 192:964 (1993)), manganese macrocyclic complexes, such as those described by Riley et al (Inorg. Chem. 35:5213 (1996)), Deune et al (Plastic Reconstr. Surg. 98:712 (1996)), Lowe et al (Eur. J. Pharmacol. 304:81 (1996)) and Weiss et al (J. Biol. Chem. 271:26149 (1996)), nitroxides (Zamir et al, Free Radic. Biol. Med. 27:7-15 (1999)), fullerenes (Lai et al, J. Autonomic Pharmacol. 17:229-235 (1997); Huang et al, Free Radic. Biol. Med. 30:643-649 (2001), Bensasson et al, Free Radic. Biol. Med. 29:26-33 (2000)), CuPUPY (Steinkühler et al, Biochem. Pharmacol. 39:1473-1479 (1990)) and CuDIPS (Steinkühler et al, Biochem. Pharmacol. 39:1473-1479 (1990)). (See also U.S. Pat. Nos. 6,084,093, 5,874,421, 5,637,578, 5,610,293, 6,177,419, 6,046,188, 5,834,509, 5,827,880, 5,696,109, and 5,403,834).

The compounds of the invention can be used alone or in combination with other agents to induce immune tolerance. As shown in the Examples that follow, the present mimetics can be used to alter events that occur during antigen presentation to lymphocytes to create a condition of immune tolerance. This process can be used in the treatment of diseases involving reaction to foreign antigens (e.g., transplantation) or self antigens (e.g., autoimmune diseases such as diabetes, multiple sclerosis, glomerulonephritis, rheumatoid arthritis and collagen vascular diseases).

The mimetics of the invention (including those in FIGS. 9 and 18, as well as those disclosed in the publications cited herein) can also be used to protect or enhance viability of cells/tissues/organs, e.g., mammalian cells/tissues/organs, including stem cells, pancreatic β cells, liver progenitor cells, and progenitor cells isolated from adult tissue harvested from cadavers. The mimetics can be used during the processes of isolation (harvesting), preservation (e.g., freezing and thawing (or "cryopreservation" which encompasses both freezing and thawing)), expansion and/or transplantation. Cells/tissues/organs treated with the present mimetics show enhanced potential in transplantation therapy. Specifically, cells/tissues/organs treated with the mimetics can be used in transplant therapy to treat, for example, diabetes, liver failure, and inherited metabolic conditions. Cells/tissues/organs used in such therapies (particularly treatment of metabolic disorders) can be genetically engineered. (By way of example, it is noted that AEOL 10112 (see FIG. 9) has been used in connection with hepatic progenitors. In this regard, the cryopreservation buffer can be supplemented with trace elements (selenium ($10^{-9}$M), copper ($10^{-7}$M), zinc ($5 \times 10^{-11}$M)) and an antioxidant (e.g., a porphyrin SOD mimetic at 10 mcg/ml; ascorbate acid, used at about 0.1 mg/ml)).

Further, the mimetics of the invention (including those in FIGS. 9 and 18, as well as those disclosed in the publications cited herein) can be used to protect cells/tissue/organs from toxicity, including free radical induced toxicity, during harvesting, preservation and transport. For example, livers, hearts and kidneys for transplant can be treated with the present mimetics.

The compounds described above, metal bound and metal free forms, can be formulated into pharmaceutical compositions suitable for use in the present methods. Such compositions include the active agent (mimetic) together with a pharmaceutically acceptable carrier, excipient or diluent. The composition can be present in dosage unit form for example, tablets, capsules or suppositories. The composition can also be in the form of a sterile solution, e.g., a solution suitable for injection (e.g., subcutaneous, i.p. or i.v.) or nebulization. Compositions can also be in a form suitable for opthalmic use. The invention also includes compositions formulated for topical administration, such compositions taking the form, for example, of a lotion, cream, gel or ointment. The concentration of active agent to be included in the composition can be selected based on the nature of the agent, the dosage regimen and the result sought. The compounds can also be encapsulated in lysosomes and thereby targeted to enhance delivery.

The dosage of the composition of the invention to be administered can be determined without undue experimentation and will be dependent upon various factors including the nature of the active agent (including whether metal bound or metal free), the route of administration, the patient, and the result sought to be achieved. A suitable dosage of mimetic to be administered IV or topically can be expected to be in the range of about 0.01 to 50 mg/kg/day, preferably, 0.1 to 10 mg/kg/day, more preferably 0.1 to 6 mg/kg/day. For aerosol administration, it is expected that doses will be in the range of 0.001 to 5.0 mg/kg/day, 0.01 to 1 mg/kg/day. Suitable doses will vary, for example, with the compound and with the result sought. The concentration of mimetic presentation in a solution used to treat cells/tissues/organs in accordance with the methods of the invention can also be readily determined and will vary with the mimetic, the cell/tissue/organ and the effect sought.

Certain aspects of the invention can be described in greater detail in the non-limiting Example that follows.

Example 1

Inhibition of Autoimmune Diabetes by Metalloporphyrin-Based Superoxide Dismutase Experimental Details
Mice NOD.scid breeding pairs were obtained either from The Jackson Laboratory (Bar Harbor, Me.) or the breeding colony at the Barbara Davis Center. NOD, NOD.scid, and BDC-2,5-TCR-Tg/NOD (2.5 TCR Tg/NOD) mice were bred and housed under specific pathogen-free conditions in the Center for Laboratory Animal Care (CLAC) at the University of Colorado Health Sciences Center.
Expansion Cultures of BDC-2.5

Expansion cultures for in vivo transfers were produced by culturing $3-6 \times 10^6$ T cells from 4-day restimulation cultures (Haskins et al, Diabetes 37:1444-1448 (1988), Haskins et al, Proc. Natl. Acad. Sci. USA 86:8000-8004 (1989)) in 60 ml complete medium (CM) and 14 U/ml IL-2. CM is DMEM supplemented with 44 mM sodium bicarbonate, 0.55 mM L-arginine, 0.27 mM L-asparagine, 1.5 mM L-glutamine, 1 mM sodium pyruvate, 50 mg/L gentamicin sulfate, 50 μM 2-ME, 10 mM HEPES, and 10% FCS. Cells were cultured in 75-cm$^2$ flasks for 4 days at 37° C. and 10% $CO_2$. T cells were harvested, washed three times, resuspended in HBSS, and injected into young (<15 days of age) NOD.scid recipients.
Metalloporphyrin Superoxide Dismutase Mimic (MnTE2PyP5+)

The SOD mimic Mn(III) tetrakis(N-ethylpyridinium-2-yl) porphyrin (MnTE2PyP5$^+$) (AEOL 10113) (SOD mimic) was obtained from Incara Pharmaceuticals. Stock solutions of 600 μg/ml in sterile HBSS for in vivo use, or 680 μM in sterile CM for in vitro experiments were prepared.
Adoptive Transfer of BDC-2.5 T Cell Clones Experimental mice were young NOD.scid mice 3-14 days of age. The recipient mice were given one i.p. injection with BDC-2.5 ($1 \times 10^7$ cells) 1 day after the administration of either the SOD mimic or HBSS as a control. The mimic or HESS was administered every other day for a total of five treatments. Urine glucose was monitored daily and when animals became diabetic, blood glucose measurements were taken. Overt diabetes was defined as a positive urine glucose (>1%), followed by a positive blood glucose test of >250 mg/dl (14 mM). Recipients were sacrificed when blood glucose readings were 320 mg/dl (18 mM) or higher. At sacrifice, the pancreata were removed for histological analysis.
Histology At sacrifice, pancreata were removed and placed in formalin for at least 24 hr. Pancreata were subsequently embedded in paraffin, sectioned, and stained with hematoxylin-eosin (H&E) to detect mononuclear cell infiltration or aldehyde fuchsin (A/F) to detect insulin.
Preparation of Purified CD4+ T Cells from 2.5 TCR-Tg/NOD Mice 2.5 TCR-Tg/NOD mice were injected i. p. with either 10 mg/kg SOD mimic or HBSS every day for 7 days. At day 8, animals were sacrificed, and the spleens were removed for isolation of CD4$^+$ T cells by immunomagnetic positive selection using the MACs magnetic cell separation kit (Miltenyi Biotec, Auburn Calif.) according to the manufacturer's protocol. The purified T cells were then plated in 96-well round-bottom plates, pre-coated with 50 µl of a 1 µM solution of a BDC-2.5 peptide mimotope, HRPI-RM, as antigen. Antigen-presenting (APC), treated with either the SOD mimic or HBSS, were added to the T cells in a crisscross fashion. The assay plates were incubated for 4 days, and then pulsed with 1 µCi of $^3$H-TdR for 6 hrs before harvesting.

T Cell and Macrophage Functional Assays

IFN-γ production by BDC 2.5 was assessed by sandwich ELISA analysis of responder T cells stimulated with α-CD3 and α-CD28, Con-A or islet cell antigen. For α-CD3/α-CD28 stimulation, 96-well round bottom plates were pre-coated with 0.125 µg/ml α-CD3 and 1 µg/ml α-CD28 for 1 hr at 37° C. After washing the plates with sterile HBSS and blocking with CM at 37° C. for 1 hr, the blocking solution was removed and the BDC-2.5 T cell clone ($2 \times 10^4$ cells) was added to the wells in the presence or absence of the SOD mimic at concentrations of 17 and 34 µM. The negative control was BDC-2.5 alone without α-CD3 and α-CD28. For Con-A stimulation, BDC-2.5 T cells were plated at $2 \times 10^4$ cells/well in 96-well flat-bottom plates with or without $5 \times 10^5$ irradiated syngeneic spleen cells as APC and Con A (2.5 µg/ml final concentration), in the presence or absence of the SOD mimic at concentrations of 17 and 34 µM. Cultures were incubated at 37° C. for 24 hr before the supernatants were harvested and assayed by sandwich ELISA for IFN-γ production. For antigen-specific recall assays, BDC-2.5 T cells were cultured in 95-well flat-bottom plates at a density of $2 \times 10^4$ cells/well, with 5000 islet-cells as antigen and $2.5 \times 10^4$ APC, in the presence or absence of 17 and 34 µM SOD mimic. Cultures were incubated at 37° C. for 48 hr before the supernatants were harvested and assayed for IFN-γ. For macrophage assays, peritoneal macrophages (PC) were harvested from unprimed NOD mice by lavage, washed 2× in sterile HBSS, and then adjusted to $5 \times 10^5$ cells/well in a 24-well plate in CM with *E. coli* LPS (055:B5) at 200 ng/ml in the presence or absence of 17 or 34 µM SOD mimic. Cultures were incubated at 37° C. for 48 hr before the supernatants were harvested and assayed by specific sandwich ELISA for TNF-α production, following the manufacturer's protocol (R&D Systems). The remaining cells were collected by trypsinization, and washed 3× in sterile PBS and 4% FCS.

Respiratory Burst of Peritoneal Macrophages

Peritoneal macrophages (PC), harvested as described above, were washed 2× in sterile HBSS and then plated ($5 \times 10^5$ cells/well) in 24-well plates in CM medium with *E. coli* LPS (055:B5) at 200 ng/ml in the presence or absence of the SOD mimic at 34 or 3.4 µM. Cultures were incubated at 37° C. for 48 hr. Cells were trypsinized and then washed to remove the trypsin and subsequently transferred to microfuge tubes. PMA was added to a final concentration of 50 ng/ml. After incubation at 37° C. for 20 min, superoxide production was assessed spectrophotometrically by ferricytochrome c reduction using an $\epsilon = 20,000$ M$^{-1}$ cm$^{-1}$, monitoring the reduction over a period of 10 min.

Determination of Beta Cell Apoptosis

In vitro apoptosis studies were conducted using the β-cell adenoma line NIT-1 (Hamaguchi et al, Diabetes 40:842-849 (1991)). Tumor cells were propagated in 75 cm$^2$ flasks at 37° C. in CM. Cell lines were re-fed with new medium every other day and were grown to confluence in the 75 cm$^2$ tissue culture flasks, at which time they were harvested using non-enzymatic Cell Dissociation Buffer (Gibco, BRL; Grand Island, N.Y.) and transferred to the appropriate culture dishes for either expansion or for the experiments described. Alloxan monohydrate (Sigma) was prepared fresh as a 0.5 M stock solution in PBS adjusted to pH 2 with hydrochloric acid. IL-1β was purchased from R & D Systems (Minneapolis Minn.). NIT-1 cells were grown to confluence in 12-well tissue culture dishes. Media was removed and replaced with PBS alone or PBS containing 34 µM mimic. All solutions were supplemented with 4% FCS. After 1 hr incubation, 10 mM alloxan was added to the appropriate wells, and cells were incubated for an additional 2 hr. For cytokine cytotoxicity assays NIT-1 cells were grown to 80% confluence in 12-well plastic tissue culture dishes. Growth media was removed and replaced with 500 µl/well of either media alone or media+34 µm mimic. After 1 hr incubation, 500 µl/well of media alone, or 20 ng/ml IL-1 (10 ng/ml final concentration)+/−34 uM SOD mimic were added. Cells were incubated an additional 48 hr, and processed. Alloxan or cytokine-treated NIT-1 cells were harvested by brief trypsinization (200 µl/well of a 12-well dish) followed by addition of 50 µl FCS to inhibit trypsin. Cells were transferred to a microcentrifuge tube and centrifuged for 5 min at 200×g. Supernatants were aspirated very carefully, leaving approximately 25 µl to allow resuspension of the cell pellets by gentle shaking of the tube. After addition of 1.3 µl of dye mix (100 µg/ml Acridine Orange+100 µg/ml of EtBr in PBS), 10 µl of cell suspension was transferred to a clean microscope slide and a coverslip placed on the suspension. Cells were scored for morphological evidence of apoptosis as described (Squier et al, Assays of Apoptosis. Humana Press, Totowa) using a fluorescence microscope with an excitation of 450-490 nm.

Statistical Analysis

Statistical significance within experiments was determined using JMP analysis software (SAS Institute, Cary, N.C.). Survival analysis was done using the product-limit (Kaplan-Meier) method. The endpoint of the experiment was defined as diabetes. Data on animals that did not become diabetic by the end of the experiment were censored. The p values shown were determined by Log-Rank test. All other statistical analysis was done by Oneway analysis of variance Anova (Wilcoxon/Kruskal-Wallis Rank Sums). If p values were ≦ to 0.05, they were considered significant.

Results

In vivo treatment of young NOD.scid mice with the SOD mimic prevents adoptive transfer of T cell mediated diabetes.

Figure 1A:
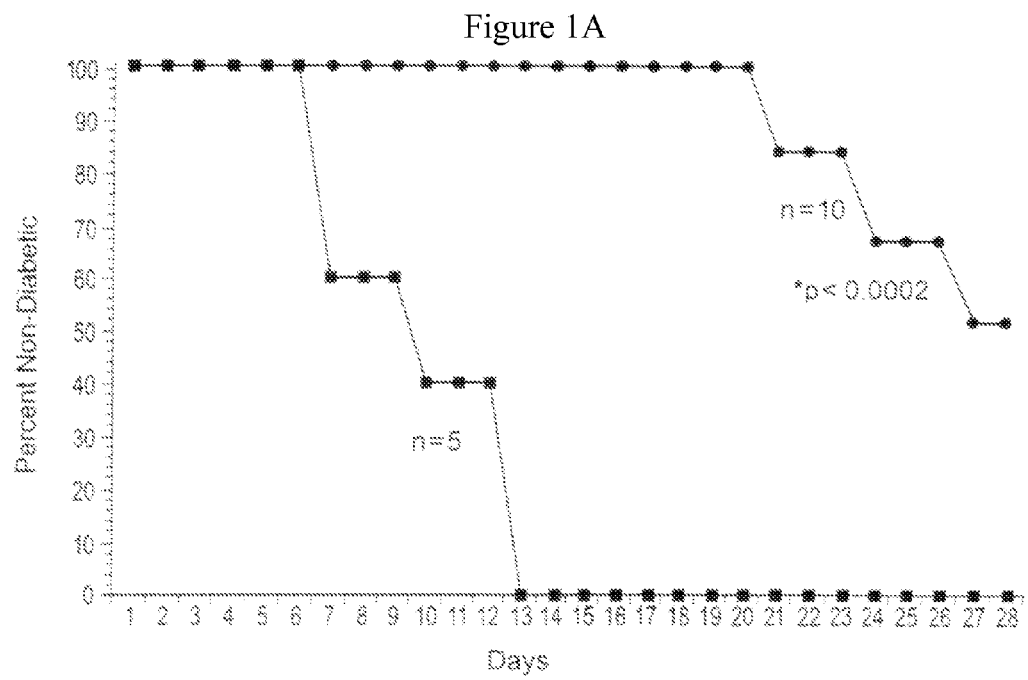
FIGS. 1A and 1B. SOD mimic administration delays or prevents T cell-mediated diabetes in young NOD (nonobese diabetic).scid (severe combined immuno-deficient) recipients after diabetogenic T cell clone BDC-2.5 transfer.
Figures 1, 1B:
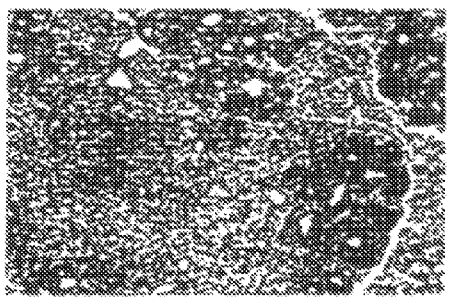
Figures 1, 1B, 2:
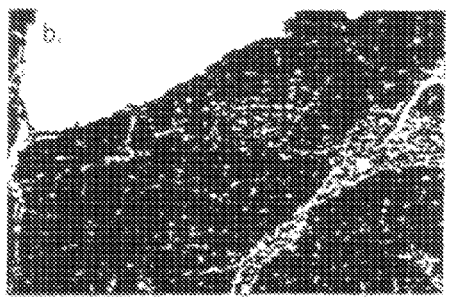

SOD mimic was delivered parenterally to NOD.scid recipients and 24 hr later, mice were adoptively transferred with the diabetogenic T cell clone BDC-2.5. The SOD mimic or HBSS was then given every other day for a total of 5 treatments. Treatment with the SOD mimic significantly delayed (p<0.0002) onset of diabetes (FIG. 1A), with 50% of the treated mice still normoglycemic after 28 days at which time all animals were sacrificed for histological examination. Pancreatic tissue from positive control animals (BDC-2.5, no SOD mimic) showed a disseminated infiltrate resembling pancreatitis, and the pancreatic architecture was almost absent (FIG. 1B-*a*). In contrast, the SOD mimic-treated animals showed an intact pancreatic architecture with few or no infiltrating mononuclear cells (FIG. 1B-b,c), as well as healthy and well-granulated islets (FIG. 1B-*d*). These data clearly demonstrate that the SOD mimic is inhibiting the infiltration by BDC-2.5 T cells and mononuclear cells to the pancreas. Remarkably, in these experiments, the animals were still protected on day 21, even though the SOD mimic was stopped on day 9, suggesting that this compound prevents priming and subsequent activation of the APC, the T-cell, or both. Longer administration of the SOD mimic may prove to be even more protective.

Interferon-gamma production by BDC-2.5 is inhibited by the SOD mimic in vitro: indirect effect on the APC leading to inhibition of T cell priming.

Figure 2A:
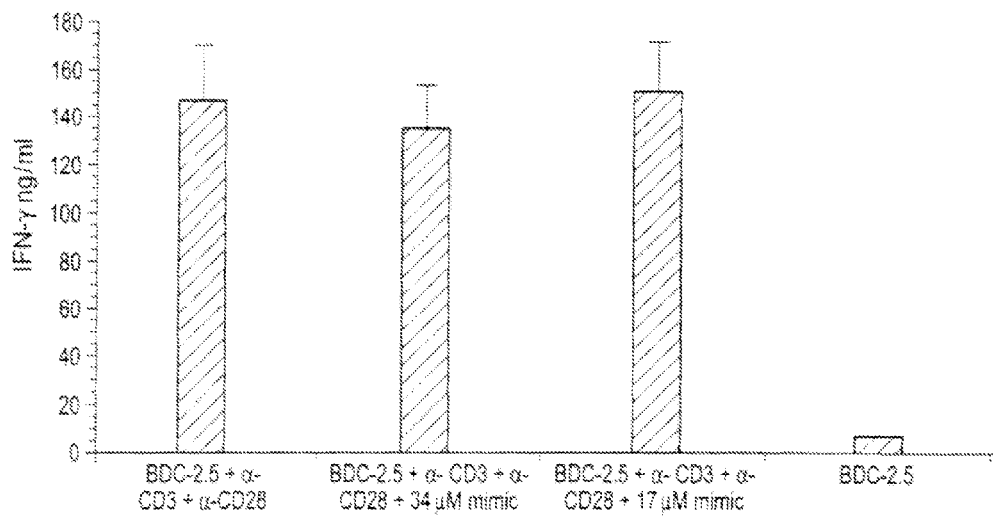
FIGS. 2A-2C. Production of IFN-γ by BDC-2.5 treated cells with SOD mimic in vitro using three types of T cell stimulation.
Figure 2B:
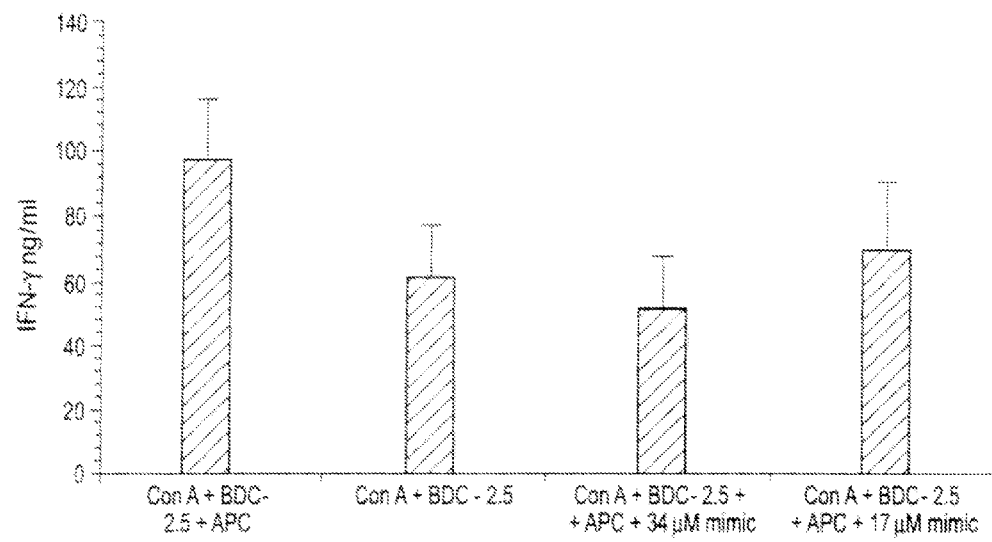
Figure 2C:
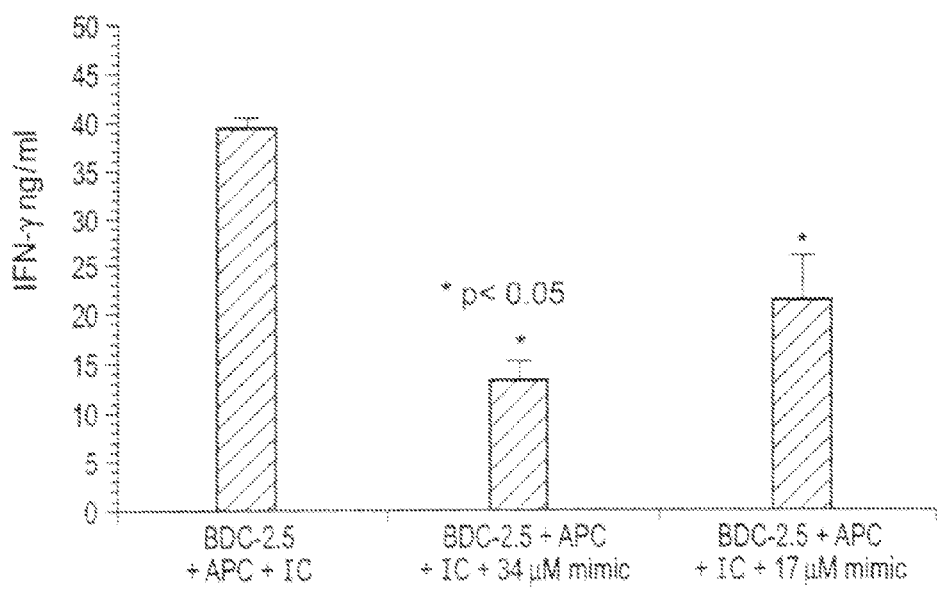
Figure 3:
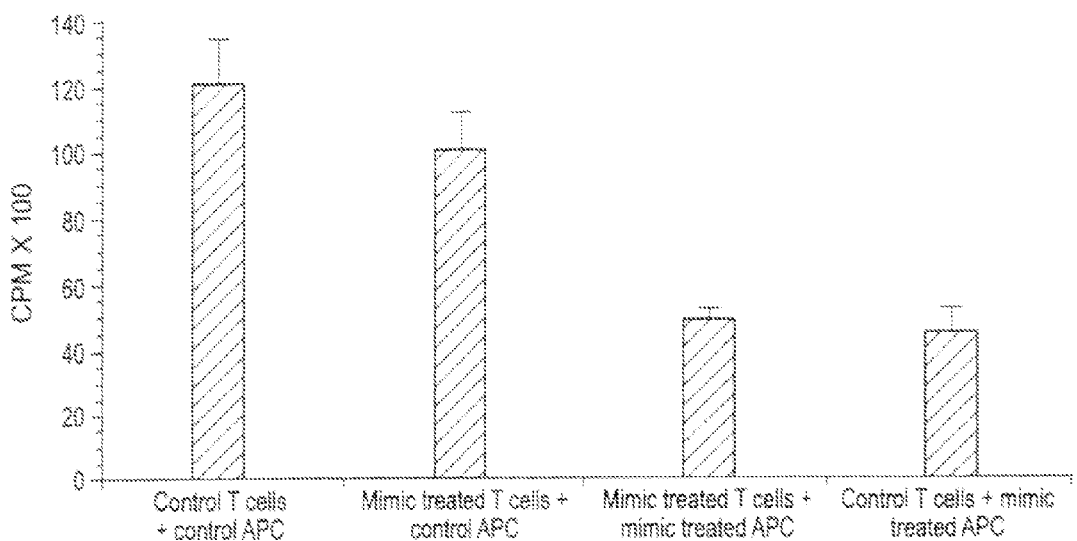

In vivo, BDC-2.5 must be primed by its antigen via presentation by APC in order to become activated and produce IFN-γ. Therefore, the SOD mimic could be directly inhibiting T cell activation or the interaction between the APC and the T cell or both. In order to elucidate the mechanism of inhibition of disease transfer, priming of BDC-2.5 was studied in vitro, in the presence or absence of APC. To determine if the SOD mimic has a direct effect on IFN-γ production by the T cell, BDC-2.5 was cultured with plate bound α-CD3 and α-CD28. This type of activation substitutes for both signals 1 and 2 of T cell activation (Mueller et al, J. Immunol. 142:2617-2628 (1989), Mueller et al, Annu, Rev. Immunol. 7:445-480 (1989), Schwartz et al, Cold Spring Harb. Symp. Quant. Biol. 54:605-610 (1989), June et al, Immunology Today 15 (1994)), thus removing the contribution of the APC. FIG. 2A shows that α-CD3 and α-CD28 stimulation resulted in no significant difference in IFN-γ production by the BDC-2.5 clone, whether or not the SOD mimic was present. These results demonstrate that when plate-bound antibodies substitute for signals 1 and 2, the SOD mimic has no direct effect on the ability of BDC-2.5 to be stimulated to effector function and produce IFN-γ. Although primed T cells can directly respond to Con A, optimal Con A-induced T-cell cytokine production requires the participation of accessory cells (e.g., macrophages) (Ahmann et al, J. Immunol. 121:1981-1989 (1978), Hunig et al, Eur. J. Immunol. 13:1-6 (1983), Hunig, Eur. J. Immunol. 13:596-601 (1983), Hunig, Eur. J. Immunol. 14:483-489 (1984), Bekoff et al, J. Immunol. 134:1337-1342 (1985), Roosnek et al, Eur. J. Immunol. 15:652-656 (1985), Hoffmann et al, Lymphokine Res. 5:1-9 (1986)). In order to determine if the SOD mimic could inhibit APC-mediated Con A stimulation of T cells, BDC-2.5 cells were incubated with Con A and APC in the presence or absence of SOD mimic. FIG. 2B shows that 34 or 17 μM SOD mimic inhibited IFN-γ production by 47 or 30%, respectively. The levels of IFN-γ produced in the presence of the SOD mimic were similar to levels seen when BDC-2.5 was incubated with Con A alone. These results indicate that the SOD mimic inhibits the ability of the APC to optimally stimulate Con A-dependent T cell activation and IFN-γ production. To further study the SOD mimic's effect on APC-T cell interactions, IFN-γ production was measured in the presence of macrophages as APC and islet cells as a source of antigen. FIG. 2C shows that when this more physiological in vitro assay was done, the ability of BDC-2.5 to make IFN-γ was reduced: the 17 μM concentration of SOD mimic inhibited by 46% (p<0.05), while the 34 μM concentration inhibited by 66% (p<0.05).

In vivo treatment of 2.5 TCR Tg/NOD mice with the SOD mimic affects T cell proliferation by inhibiting APC function.

Figures 1, 1B, 2, 3:
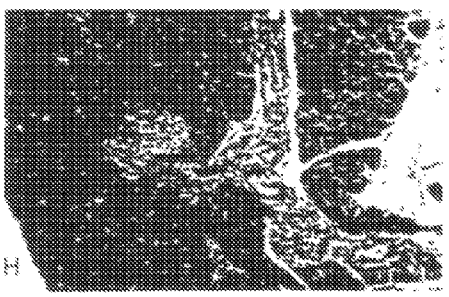
FIG. 3. In vivo treatment of 2.5 TCR Tg (transgenic)/NOD mice with the SOD mimic. 2.5 TCR-Tg/NOD mice were treated for 7 days with 10 mg/ml SOD mimic or HBSS. Spleen cells were harvested from the animals on day 8 and the T cells were purified from SOD mimic or control mice and plated ($6 \times 10^4$ cells/well) with APC ($3 \times 10^5$ cell/well) from either SOD mimic or control mice in a criss-cross fashion. The cultures were pulsed with 1 μM of HRPT-RM peptide and on day 4 of culture, the plate was pulsed with (1 μCi $^3$H-TdR) for 6 hr before harvest. Values are the mean and SEM of triplicate wells. Data are representative of duplicate experiments.
Figures 1, 1B, 2, 3, 4:
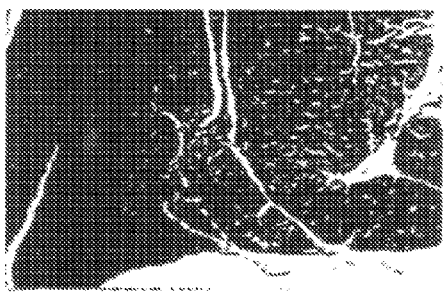

In order to determine if the SOD mimic can influence T cell priming in vivo, 2.5 TCR-Tg/NOD mice, which carry the rearranged TCR genes of the BDC-2.5 T cell clone (Katz et al, Cell 74:1089-1100 (1993)), were treated with either the SOD mimic (10 mg/kg) or HBSS each day for 7 days. The T cells and APC were purified from SOD mimic-treated and control mice and cultured in a crisscross proliferation assay using a peptide mimotope HRPI-RM that acts as a stimulating antigen for the 2.5 TCR-Tg cells. FIG. 3 demonstrates that APC from SOD mimic-treated mice showed a reduced ability to support T cell proliferation whether they are presenting the peptide to SOD mimic-treated or untreated T cells. Notably, when control APC were used as presenters, the proliferative response in SOD mimic-treated T cells approached the level achieved with control APC and T cells. These data demonstrate that in vivo SOD mimic treatment inhibits the response in TCR-Tg mice primed to a specific self-peptide and indicate that using the SOD mimic in combination with candidate autoantigens may provide a form of antigen-specific tolerance.

LPS-induced respiratory burst and cytokine production by peritoneal macrophages is inhibited by the SOD mimic.

Figure 4A:
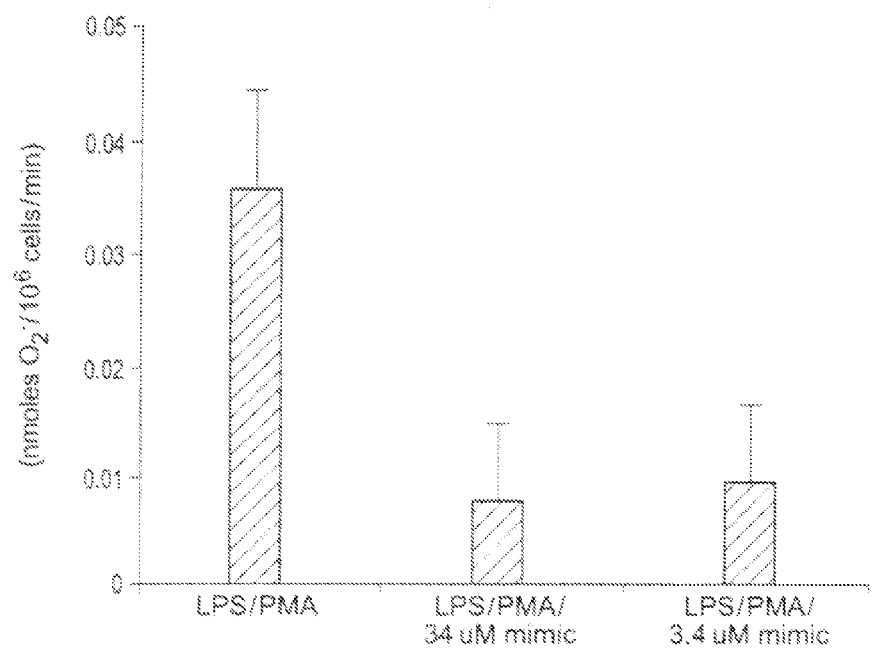
FIGS. 4A and 4B. LPS (lipopolysaccharide)-induced respiratory burst and cytokine production by peritoneal macrophages.
Figure 4B:
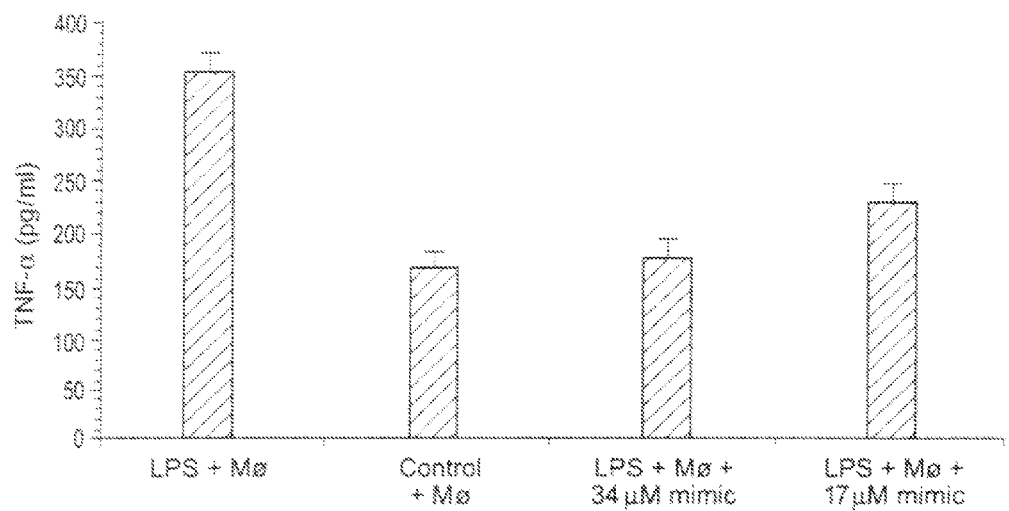

Macrophages are activated in the two-stage reactions of priming and triggering (Meltzer, J. Immunol. 127:179-183 (1981)). In order to assess the inhibitory effect of the SOD mimic on this process, peritoneal macrophages (PC) were cultured with LPS in the presence or absence of the mimic. The supernatants were collected and the PC (peritoneal macrophages) were washed and triggered with PMA to measure their NADPH oxidase-mediated respiratory burst and superoxide production. FIG. 4A shows that 3.4 μM SOD mimic results in a 75% reduction in superoxide production and increasing the concentration of SOD mimic to 34 μM did not significantly further decrease superoxide production. Moreover, FIG. 4B shows that TNF-α production by LPS-primed PC was inhibited 34% by 17 μM mimic, while 34 μM mimic resulted in a 51% inhibition. These data clearly demonstrate that pre-incubation of LPS-primed macrophages with SOD mimic inhibited both activation of NADPH oxidase and TNF-α production. It should be noted that the SOD mimic had been washed off prior to the assay and, therefore, was not present in the extracellular space where superoxide generation is measured. Therefore, a decrease in superoxide production was not due to the SOD mimic scavenging the extracellular superoxide but rather to a reduction in oxidase-dependent superoxide. The fact that superoxide production by activated macrophages (FIG. 4A) is inhibited by 3.4 μM SOD mimic, while inhibition of TNF-α or IFN-γ production requires higher SOD mimic concentration (FIG. 4B, 2C), indicates that the oxidant concentration necessary to activate the NADPH oxidase of macrophages is lower than the oxidant concentration necessary to activate the signal transduction pathways required for cytokine production. These results point to the fascinating prospect that biological responses to oxidants are not just "all-or-none", but instead are specific to the pathway involved.

SOD mimic-treated NIT-1 insulinoma cells are protected from alloxan and cytokine-mediated cytotoxicity.

Figure 5A:
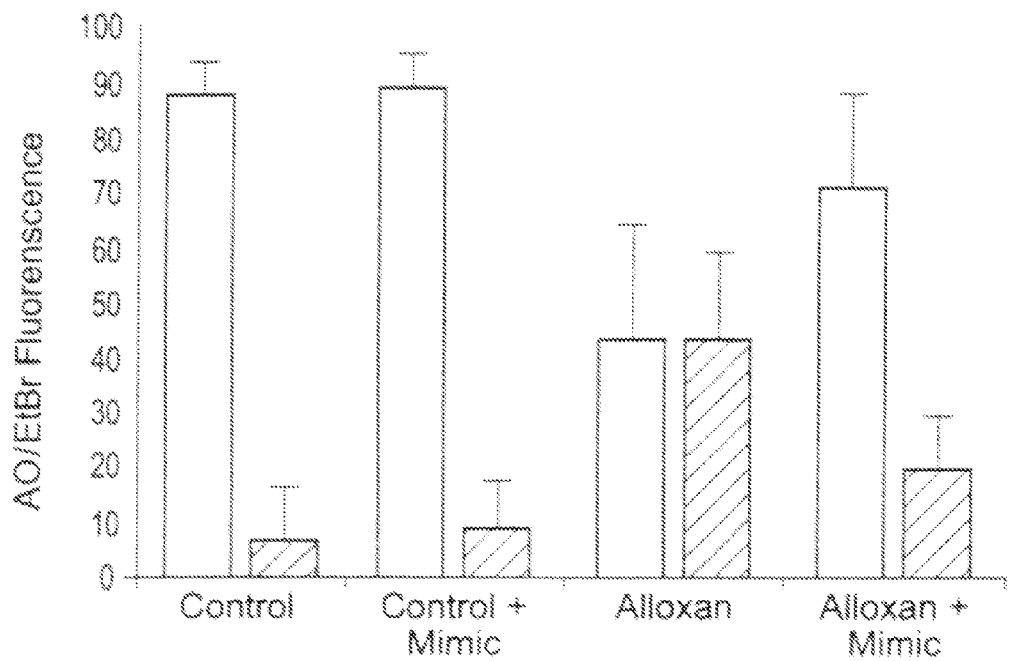
FIGS. 5A and 5B. Alloxan and cytokine cytotoxicity of SOD mimic treated NIT-1 cells.

Both alloxan and pro-inflammatory cytokines have been shown to be cytotoxic to β-cells in vitro. This series of experiments was designed to determine if the SOD mimic could protect islet cells from alloxan and cytokine-mediated cytotoxicity using the well established NIT-1 insulinoma cell line. FIG. 5A shows that incubation of NIT-1 cells with 10 mM alloxan induces 50% apoptosis compared to 5% for control untreated or control plus SOD mimic. However, NTT-1 cells exposed to alloxan and treated with the SOD mimic show 70% viability.

Figure 5B:
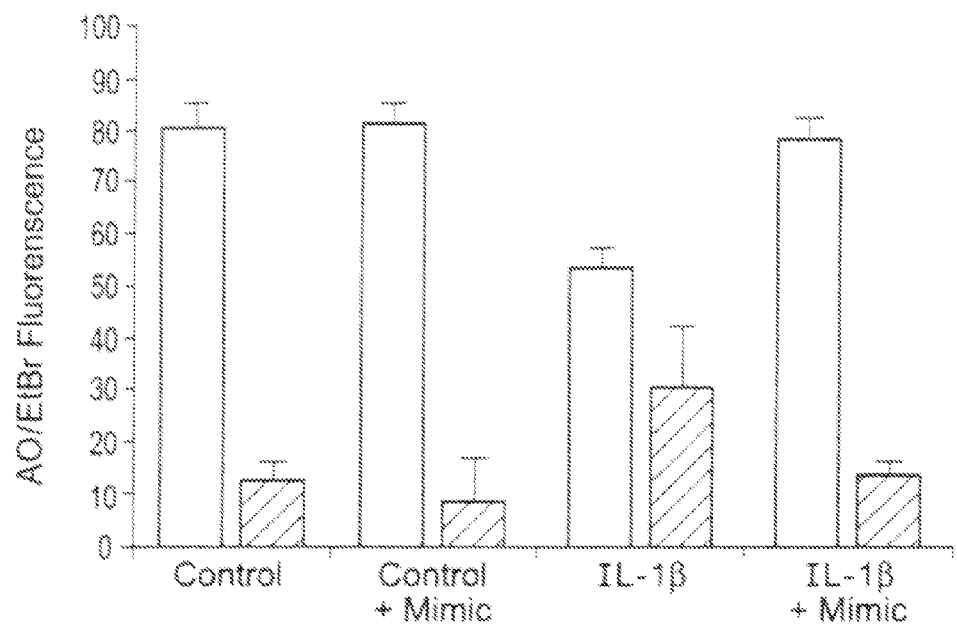

FIG. 5B demonstrates the protective effect of the SOD mimic on NIT-1 cells exposed to IL-β in culture. The addition of 10 ng/ml IL-1β was cytotoxic to NIT-1 cells (~50% of the cells were apoptotic) compared to control or control plus SOD mimic. A clear protective effect was seen when NIT-1 cells exposed to IL-1β were treated with SOD mimic. The SOD mimic's protective effect is consistent with other reports of antioxidant proteins conferring resistance to immunological damage in insulinoma cells (Grankvist et al, Biochem. J. 199:393-398 (1981), Malaisse et al, Proc. Natl. Acad. Sci. USA 79:927-930 (1982), Lenzen et al, Free Radic. Biol. Med. 20:463-466 (1996), Tiedge et al, Diabetes 46:1733-1742 (1997), Benhamou et al, Diabetologia 41:1093-1100 (1998), Tiedge et al, Diabetes 47:1578-1585 (1998), Tiedge et al, Diabetologia 42:849-855 (1999)).

Example 2

Protection from Streptozotocin-Induced Diabetes and Facilitation of Islet Engraftment by SOD Mimetic Treatment 1: Protection from streptozotocin-induced diabetes by in vivo treatment with SOD mimetic.

Experiment:

Diabetes was induced in C57Bl/6 male mice with 160 mg/kg streptozotocin (SZ) intravenously. Recipients were either otherwise untreated or were treated with daily intraperitoneal bolus injections with 1 mg/kg or 10 mg/kg of the SOD mimetic on days −1 through +5 relative to SZ treatment.

Figure 6:
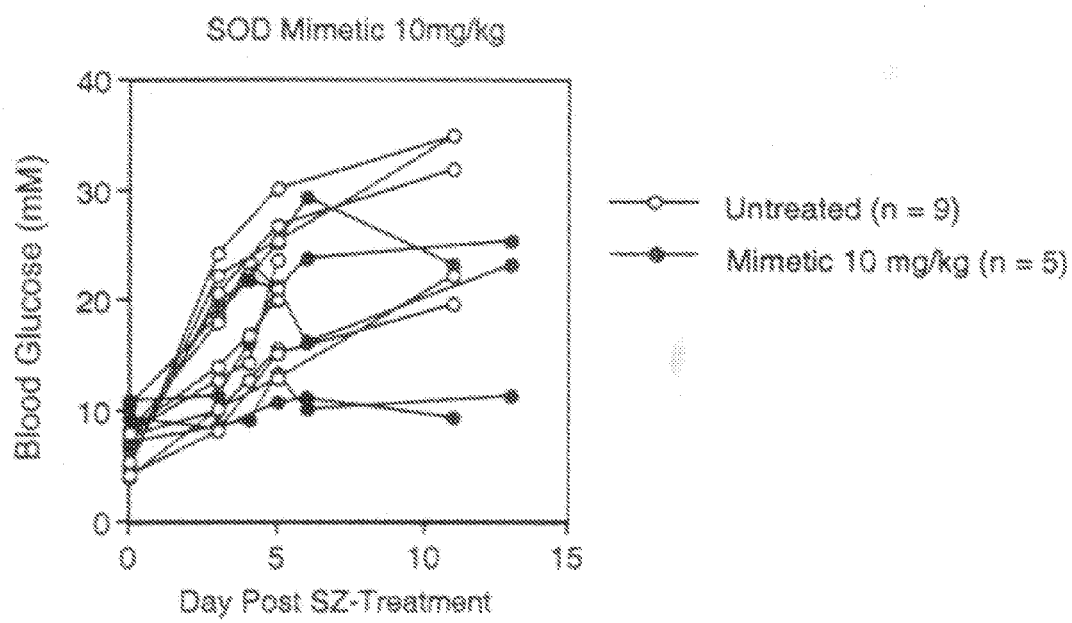
FIG. 6. Protection from streptozotocin-induced diabetes by in vivo treatment with SOD mimetic (AEOL 10113).

Results:

1 mg/kg of the mimetic demonstrated some protection from SZ-induced diabetes. Results indicate that the 10 mg/kg dose led to protection in 2/5 animals (versus 0/9 in untreated animals). (See FIG. 6.)

2: Protection of islet transplants from streptozotocin-induced diabetes by in vitro culture with SOD mimetic.

Experiment:

Syngeneic C57Bl/6 islet grafts were pre-treated in vitro with SOD mimetic (34 µM) for 2 hours and then transplanted in C57Bl/6 challenged with 160 mg/kg SZ as described above.

Figure 7:
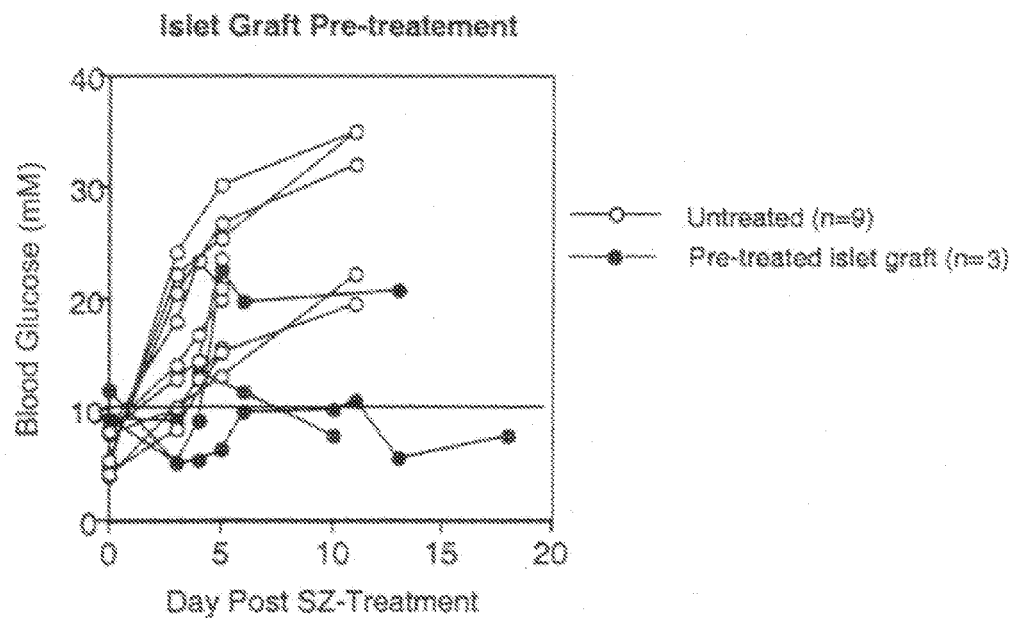
FIG. 7. Protection of islet transplants from streptozotocin-induced diabetes by in vitro culture with SOD mimetic.

Results:

Pre-treatment of the islet graft prior to transplant led to protection in 2/3 islet grafts. (See FIG. 7.)

3: Facilitation of islet engraftment in spontaneously diabetic NOD mice by in vitro pre-treatment with SOD mimetic.

Experiment:

Recurrence of disease in autoimmune diabetic NOD mice is so vigorous that islet transplants often fail to engraft (i.e., grafts fail to restore even transient euglycemia). This experiment determined whether initial inflammatory damage to syngeneic NOD islet grafts could be attenuated by treating NOD islets in vitro with a SOD mimetic prior to transplant. Syngeneic NOD islet grafts were pre-treated in vitro with SOD mimetic (34 µM) for 2 hours and then transplanted into spontaneously diabetic (autoimmune) NOD recipient.

Figure 8:
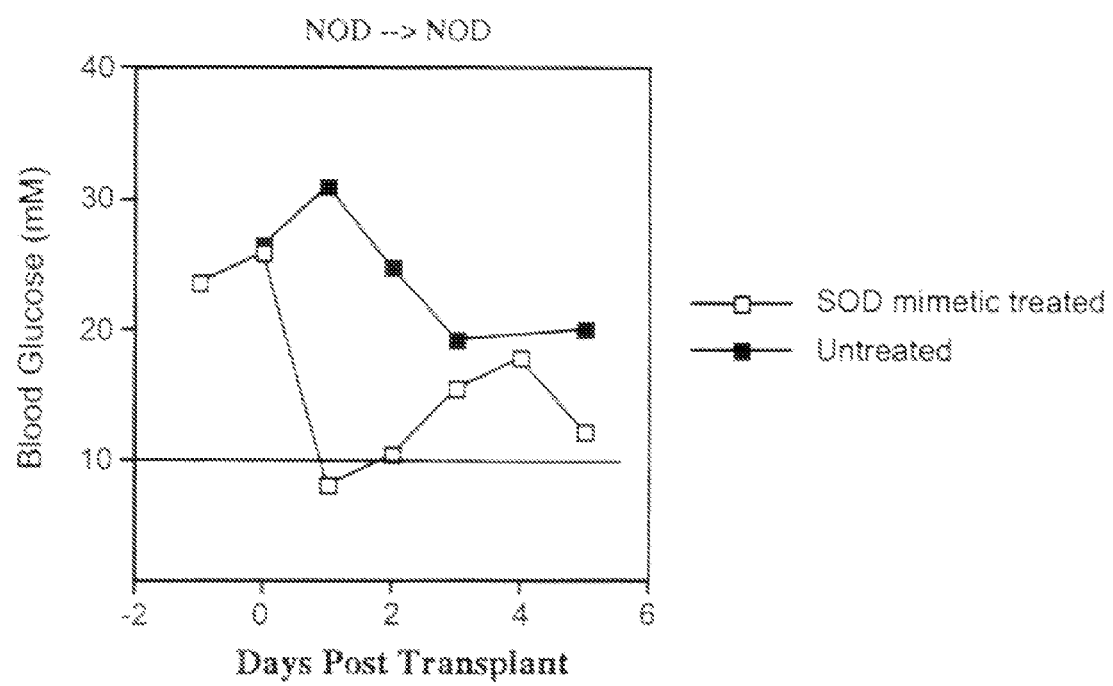
FIG. 8. Facilitation of islet engraftment in spontaneously diabetic NOD mice by in vitro pre-treatment with SOD mimetic.

Results:

The treated NOD islet graft restored euglycemia within 24 hours relative to the untreated control NOD graft that failed to engraft during the initial 5 day observation period. (See FIG. 8)

Example 3

Human Islet Isolation

Islets are obtained from the pancreas of cadaveric donors (islets comprise approximately 1-2% of the pancreas). The donor pancreas is harvested and preserved with UW (University of Wisconsin solution, DuPont Pharma, Wilmington, Del.). An automated method is used to isolate islets from the donor pancreas (Ricordi et al, Diabetes 37:413-420 (1988), Tzakis et al, Lancet 336:402-405 (1990)). All procedures are performed under aseptic conditions in Class II biohazard hoods or clean roams with solutions comprised of sterile components.

The pancreas is removed from the shipping container and placed into a sterile tray containing 500 ml a cold preservation solution. A sample of the preservation solution is taken for microbiological analysis. This tray is placed in a larger tray and maintained cold via a cold bath or using 1 L of cold sterile ice (from 2 L of frozen sterile water); the organ is trimmed of fat and non-pancreatic tissue and weighed. After cleaning, the pancreas is dipped in betadine and antibiotics and the tray containing the pancreas is removed from the ice for the distension procedure.

The pancreatic duct is cannulated with catheters and the pancreas is distended with sterile filtered collagenase solution. The collagenase solution consists of Liberase-HI (Roche Molecular, Indianapolis, Ind.) dissolved in 15 ml Hank's Balanced Salt Solution and diluted to a maximal total volume of 350 ml. Liberase-HI has been specifically formulated for use in human islet isolation procedures (Linetsky, Diabetes 46:1120-1123 (1997)).

The distended pancreas is placed into a sterile stainless steel chamber (Ricordi et al, Diabetes 37:413-420 (1988), Tzakis et al, Lancet 336:402-405 (1990)), additional collagenase solution is added, and the collagenase solution is recirculated and brought to 37° C., as the chamber is mechanically agitated (Ricordi et al, Diabetes 37:413-420 (1988), Tzakis et al, Lancet 336:402-405 (1990)). During this digestion procedure, samples are taken at intervals to monitor the breakdown of the pancreas via microscopy. The length of digestion varies but in general, once the temperature has reached 37° C. inside the chamber and most of the islets are free of the surrounding acinar tissue (15-25 minutes) the digestion process can be stopped.

Once free islets are detected, the recirculation cylinder and the heating circuit are bypassed and the islet separation is conducted in a system in which the temperature is progressively decreased and the collagenase solution is diluted with solutions. The digest containing the free islets is collected into sterile containers at 42° C. to prevent enzymatic overdigestion. An aliquot of the digest (composed of endocrine and acinar tissue) is taken for staining with dithizone; the percentage of free islets, degree of islet fragmentation, and the condition of the acinar tissue are noted. The tissue is centrifuged and recombined and the supernatant removed. The pellets are collected and resuspended in tubes containing UW and held on ice for 30 minutes before proceeding with purification steps. UW allows acinar cells to reestablish osmotic equilibrium, hence preventing cell swelling. This procedure is aimed at increasing the difference in density between islets and acinar tissue, a key parameter for effective purification based on difference in density (Robertson, Br. J. Surg. 79:899902 (1992)).

The separation of islets from exocrine tissue is performed via density gradient centrifugation in a COBE 2991 blood cell processor (Ricordi et al, Diabetes 37:413-420 (1988), Tzakis et al, Lancet 336:402-405 (1990)$_2$). The gradients are composed of dissolved sugar gradients (Ficoll) dissolved in Eurocollins solution, using defined protocols. After collection of the resulting fractions from the COBE 2991, islet enriched fractions (purity=islets Vs non islets ~60-90%) are washed extensively to remove Ficoll and resuspended in culture medium composed of CMRL plus 10% FCS, antibiotics and L-glutamine.

The islet cell suspension may be cultured prior to transplant. Groups of islets are placed in a 22° C. incubator (95% air, 5% $CO_2$) in MCRL 1066 media supplemented with 10% FCS, 1% HEPES, 1% glutamine, and 1% antibiotic solution and filtered with a 0.2 m filter. After suspension in culture media, and immediately prior to placement in the incubator, representative aliquots of islets will be removed for bacteriology and mycology assessment, for enumeration, and for assessment of viability, endotoxin content, and functional capacity.

Prior to transplantation, the islets are collected from the tissue culture flasks/bags and placed into tubes, a sample of the culture media is taken for mycoplasma testing, and the suspension is centrifuged. The islets are resuspended in transplant media (TX media: HBSS, 2.5% human serum albumin, HAS) and centrifuged to wash out cellular debris, tissue culture media (FCS) and, soluble proteolytic activity. The islets are resuspended once more in TX media, aliquots are removed for islet enumeration and microbiology, and the cells are centrifuged again. A sample is taken from the supernatant for microbiological analysis, and the islets are suspended in 200 ml of TX media for transplant.

In order to determine the functional capacity of the preparation, two aliquots of freshly isolated for cultured islets will be incubated overnight at 37° C. On the subsequent morning, standard techniques for static incubation and assessment of insulin release, DNA content, and insulin content will be utilized to determine the functional capacity of the islets (Ricordi et al, Diabetes 37:413-420 (1988), Tzakis et al, Lancet 336:402-405 (1990)). Briefly, samples will be washed twice in basal media (RPMI 1640+10% FBS) containing 2.8 mM glucose, followed by a 2-hour incubation in, basal medium and a further 2 washes. One aliquot will then be incubated in basal medium and one in medium containing 16.7 mM glucose to assess glucose mediated insulin release. At the end of the incubation period, media will be collected and frozen at −20° C. until they are assayed for immunoreactive insulin. The islets will be washed twice in basal media, and acid alcohol will be added for a period of 18 hours to assess islet insulin content. Standard RIA procedures will be used to determine insulin content.

Example 4

Figure 10:
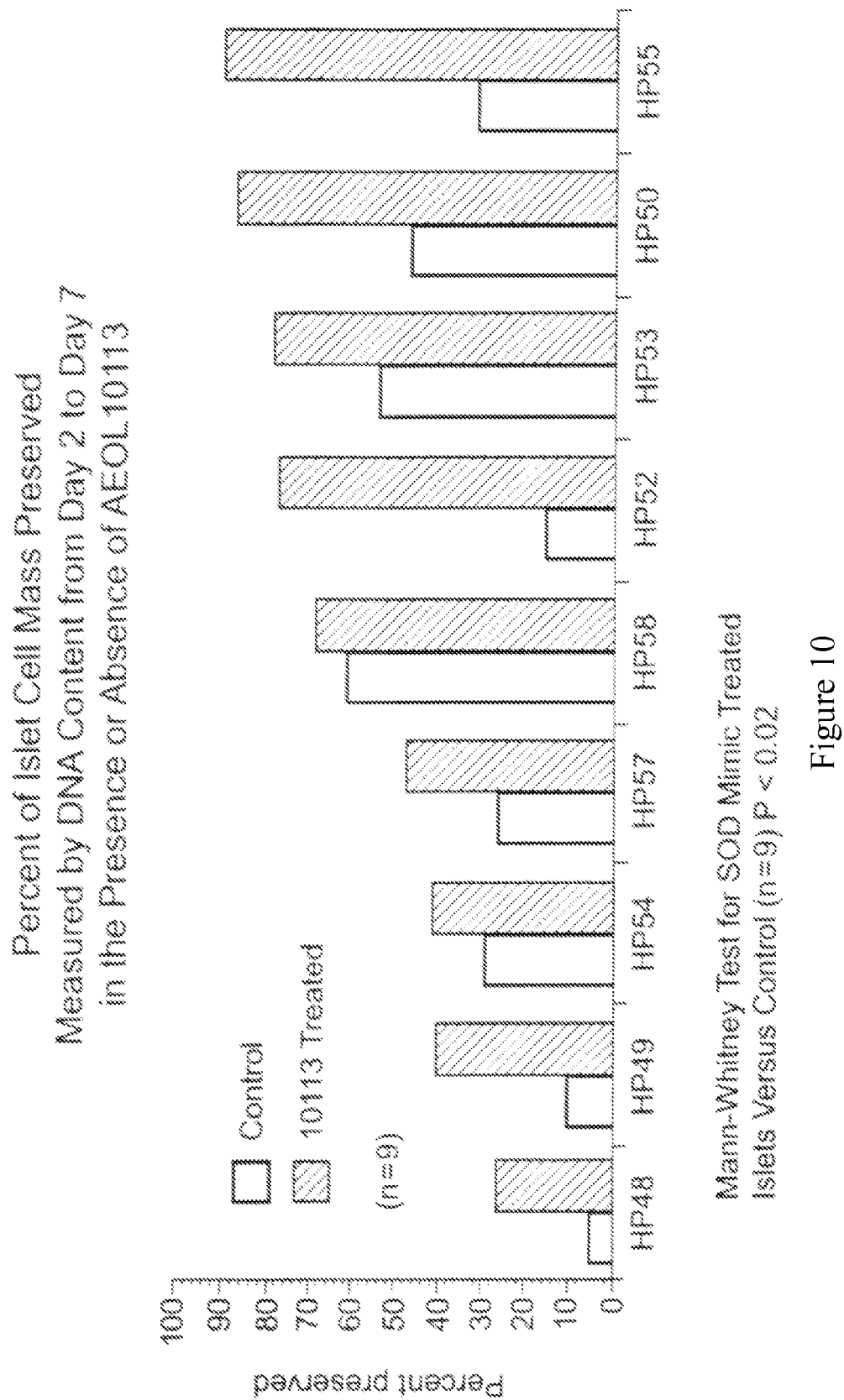
FIG. 10. Percent of islet cell mass preserved measured by DNA content from day 2 to day 7 in the presence or absence of AEOL 10113.
Figure 11:
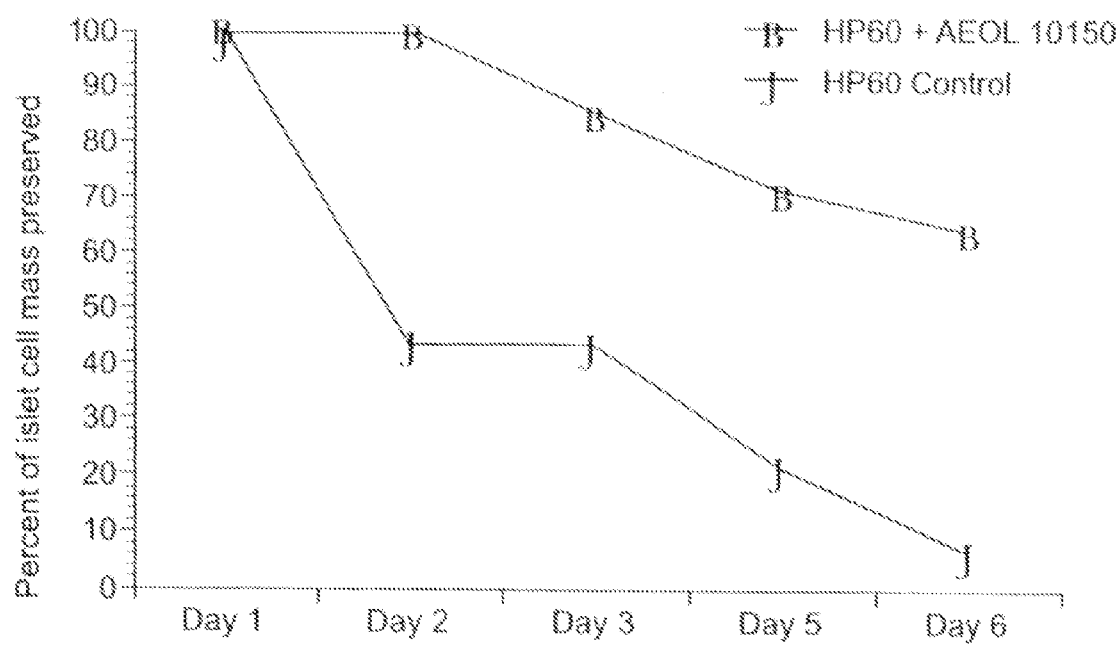
FIG. 11. Addition of the SOD mimic AEOL 10150 to liberase during digestion procedure increases human islet cell mass as compared to control.

Preservation of Human Islets after Isolation Using a Metalloporphyrin-Based Superoxide Dismutase Mimic Islet transplantation is an attractive alternative to chronic insulin administration for the restoration of normoglycemia in type I diabetes. However, that single cadaveric donors do not provide sufficient numbers of islets to achieve insulin independence in recipients erects a stumbling block. One reason for the limited number of islets obtained after isolation could be due to the loss of cells by apoptosis during and after isolation. In this study, it was demonstrated that incubation of human islets, from cadaveric donors (n=5), for 6 days in a free-radical scavenging, metalloporphyrin-based superoxide dismutase mimic Mn(III) tetrakis (N-ethylpyridium-2-yl) porphyrin (SOD mimic), exhibited a 3-fold increase in beta cell mass compared to control islets as measured by DNA content. The increase in beta cell mass correlated with an increase in overall cell viability. Dithizone staining throughout the 6 day incubation period revealed that all preparations maintained at least 75% of islet mass. There was no detectable loss of beta cell function in SOD mimic-treated islets as measured by static glucose stimulated insulin release. The ability of the SOD mimic to efficiently scavenge free radicals and protect cells from oxidative stress and apoptosis warrants their use for the preservation of beta cells during islet isolation procedures. (See FIGS. 10 and 11.)

Example 5

Figure 12A:
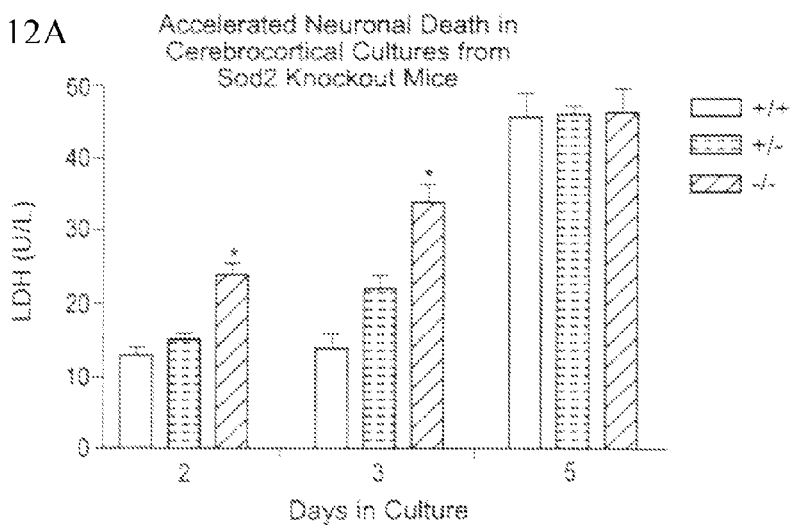
FIGS. 12A-12C. Accelerated neuronal death in cerebrocortical cultures from SOD2 knockout mice.
Figure 12B:
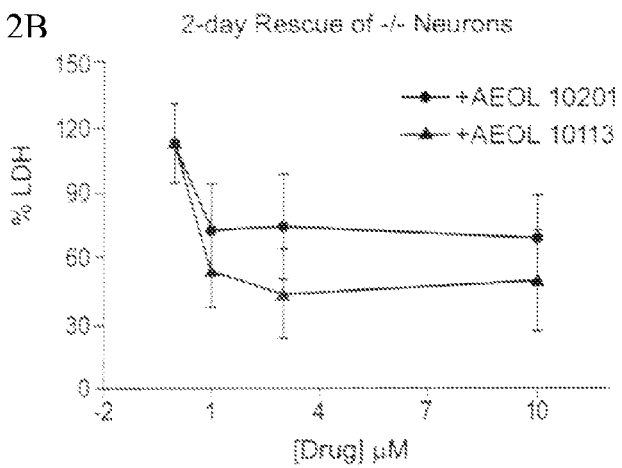
Figure 12C:
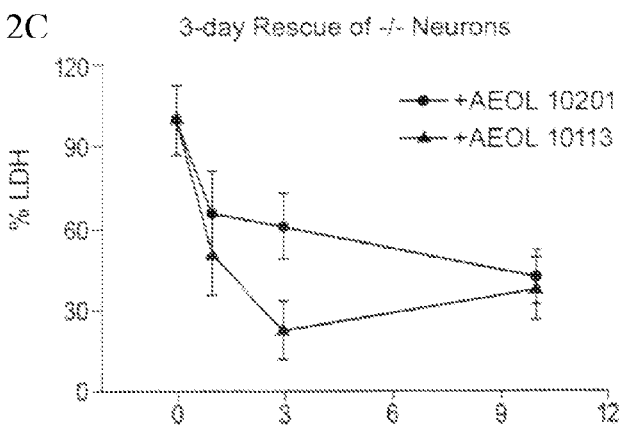
Figure 13A:
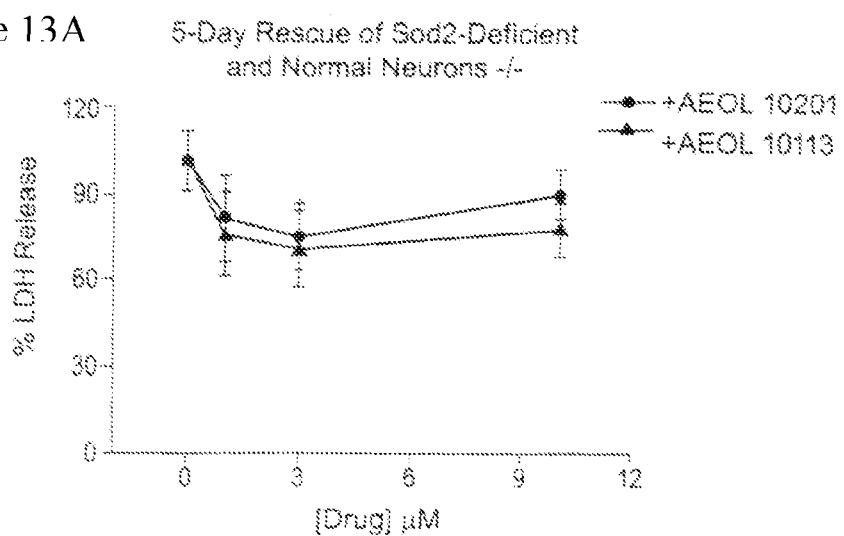
FIGS. 13A-13C. 5-Day rescue of SO D2-deficient and normal neurons. AEOL compounds increase neuronal survival of +/− and +/+ (normal) neurons 5 days after media change to serum-free conditions.
Figure 13B:
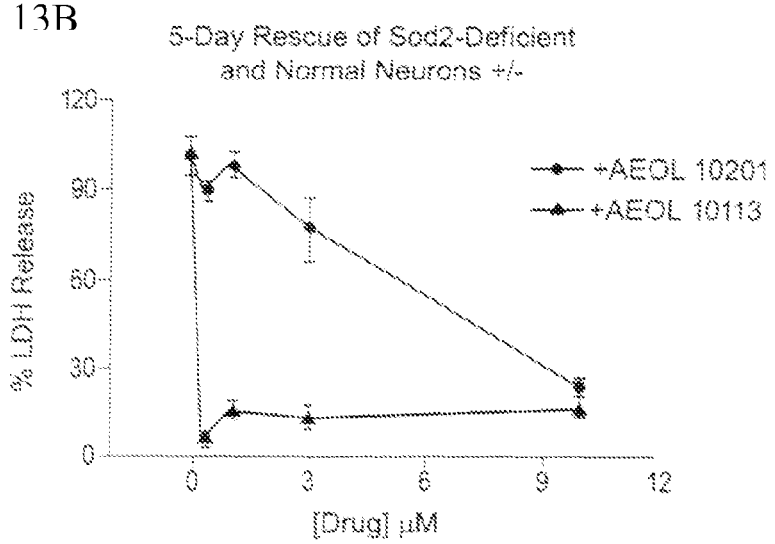
Figure 13C:
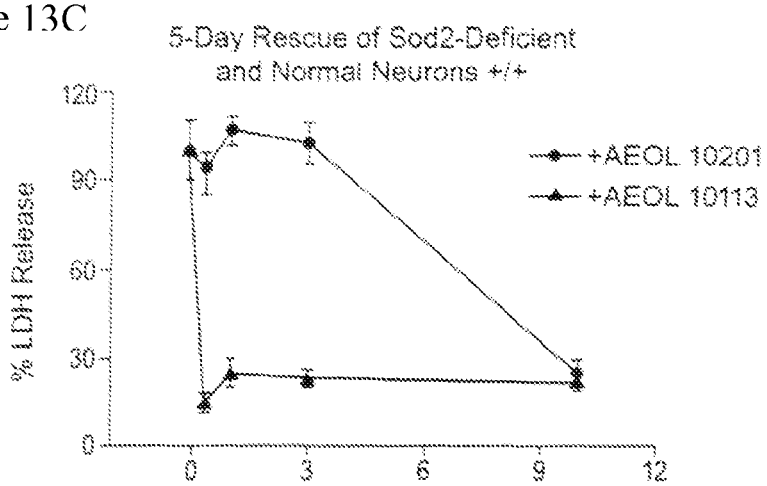

AEOL 10113 and MnTBAP (AEOL 10201) Improve the Survival of Cultured Neurons in Serum-Free Media The ability of AEOL 10201 and AEOL 10113 to improve the survival of normal and SOD2-deficient cerebrocortical neurons in primary culture was studied. Neuronal cultures were prepared from cerebral cortices of SOD2 knockout (homozygous−/−, heterozygous−/+ or wild-type+/+ genotypes) mice of embryonic days 14-16. Neuronal cultures were initially plated in serum containing minimum essential medium (MEM with Earle's salts) in a low oxygen environment (5% $O_2$, 95% Argon) for 18 hours. The presence of serum during this initial period promotes adherence of neurons to the substrate and the low oxygen levels protect SOD2-deficient neurons from ambient oxygen levels. Following this plating procedure, culture media was replaced with serum-free MEM containing vehicle or varying concentrations of AEOL compounds and placed in a normal oxygen environment. Cultures were observed for injury and supernatant media assayed for the release of lactate dehydrogenase 2, 3 and 5 days following the addition of drugs. SOD2−/− cultures showed accelerated cell death in serum-free conditions and under ambient oxygen (FIG. 12A). Neuronal cultures from SOD2+/+ and wild-type (normal) mice died from serum-deprivation 5 days following media change. AEOL 10201 and 10113 improved the survival of SOD2−/− cultures on days 2, 3 and 5 (FIGS. 12B, 12C and FIG. 13A). AEOL 10201 and 10113 dramatically improved the survival of wild-type (normal) and SOD2+/− cultures 5 days after media change to serum-free conditions. These results indicate that AEOL 10113 and 10201 can substitute for the presence of protective factors in serum that promote cell survival. They further indicate than catalytic antioxidants can be used for maintaining cultured cells in serum-free media.

Example 6

Preservation of Human Islet Cell Function Mass

Experimental Details
Human Islets

Human pancreata were obtained from CORE (Center for Organ Recovery and Education-Pittsburgh) and from NDRI (National Disease Research Interchange—Philadelphia). Twelve pancreata failing the standard criteria for the use of whole pancreas or islet transplantation were processed (Table 1). To more comprehensively test the compound, it was set up to utilize all available organs without applying any exclusion criteria. The cold ischemia time was 9±2 hr ranging from 5 to 15 hr. The age was 49±4 years (range 17-68 years) and body mass index 26±2 (values are mean±SEM). The final islet yield (IEQ/g) for the pancreatic preparations (n=9) obtained with the semi-α utomated method, which consisted of purity between 60-80%, was 4628±749 IEQ/g range 1790 to 7631, median 4542.

The percentage of islets over whole preparation was determined immediately after isolation, by dithizone (Sigma, St. Louis, Mich.) staining (Latif et al, Transplantation. 45:827-830 (1988). This was 60-80% in the first group of nine islet preparations and respectively 60%, 60%, and 30% in the last three preparations. The yield obtained using the second series of experiments (stationary digestion) was 1744±676 IEQ/g.

TABLE 1

Donor Characteristics

| Human Pancreas (HP) | Age | Cold Ischemia Time | Gender | Body Mass Index | % islets/ whole preparation |
|---|---|---|---|---|---|
| Study group 1 | | | | | |
| 48 | 68 | 7 | M | 22.9 | 60-70 |
| 49 | 50 | 15 | F | 30.2 | 60-70 |
| 50 | 54 | 5 | M | 27.7 | 65-75 |
| 52 | 49 | 12 | M | 30.4 | 65-75 |
| 53 | 51 | 8 | F | 17.6 | 60-70 |
| 54 | 46 | 6 | F | 17.6 | 70-80 |
| 55 | 17 | 8 | F | 24.2 | 70-80 |
| 57 | 65 | 7 | F | 23.4 | 60-65 |
| 58 | 55 | 7 | M | 22.4 | 60-70 |
| Study group 2 | | | | | |
| 60 | 24 | 11 | M | 31 | 60-65 |
| 68 | 48 | 9 | F | 37 | 60-65 |
| 71 | 57 | 10 | M | 29 | 30-35 |

Culturing of Purified Human Islets in the Presence of SOD-Mimic

The initial series of experiments involved the addition of SOD-mimic after islet isolation, as a culture supplement. Metalloporphyrin SOD-mimics AEOL 10113, AEOL 10150 were provided by Incara Pharmaceuticals. The islets were isolated using the method described by Ricordi et al (Ricordi et al, Diabetes 38 Suppl 1:140-142 (1989) with minor modifications. Prior to purification, the digest was incubated in cold UW solution for 45 minutes. The islet-enriched fractions were purified using discontinuous Euro-ficoll density gradients and processed in a COBE 2991 Cell Separator (Gambro, Lakewood, Colo.). The islets were cultured for 7 days (37° C., 5% $CO_2$) in CMRL-1066 culture medium supplemented with 10% heat inactivated fetal calf serum, 100 units/ml penicillin and 0.1 mg/ml streptomycin, and 2 mmol/1 L-glutamine (Life Technologies, Grand Island, N.Y.) with or without SOD-mimic at the final concentration of 34 µmol/l. Fresh culture medium (with or without SOD-mimic) was replaced three times per week and islet samples were taken for assessment of DNA content and for functional studies at selected time points.

Determination of Islet Cell Mass and Viability

DNA content has been used as an indirect measure of cell mass, since the clustered nature of the islets, together with the non-endocrine contaminants, makes direct counting inappropriate (Ling et al, *J Clin Invest* 98:2805-2812 (1996)). DNA content was measured in samples of the islet preparations from both control and SOD-treated groups, using a Pico Green dsDNA Quantitation Kit following the manufacturer protocol (Molecular Probes, Eugene, Oreg.). Islet viability was determined by simultaneous staining of live and dead cells using a two-color fluorescence assay (Calcein-AM and Propidium Iodide, Molecular Probes) (Lorenzo et al, *Nature* 36:756-760 (1994)). The percentage of viable and dead cells was estimated in both control and SOD-treated groups.

Static Glucose Challenge and Insulin Content Measurement

Handpicked islets from control and SOD-treated groups were subjected to static glucose challenge in Krebs-Ringer bicarbonate buffer (KREBB) (pH 7.35) containing 10 mmol/l HEPES and 0.5% bovine serum albumin (Sigma). After conditioning, the islets were incubated in KRBB containing low (2.8 mmol/l) and high (20 mmol/l) glucose concentrations for one hour. At the end of the glucose challenge, insulin extraction was carried out to determine islet insulin content (Pipeleers et al, *Diabetes* 40:908-919 (1991)). The insulin levels were measured by ELISA (ALPCO, Windham N.H.).

Immunocytochemistry

Samples of the purified islet preparations were fixed in Bouin's solution for one hour and then transferred to 10% buffered formalin. Using standard procedures, the islet samples were stained for immunoreactive pro-insulin, glucagon, CK19 (Scytek Laboratories, Logan, Utah) and amylase (Biogenex, San Ramon, Calif.) and the percentage of positive cells was counted in both control and SOD-treated groups.

Perifusion Protocol of Islet Insulin Release

Whether addition of SOD-mimic to the islet medium induces unregulated insulin release, this was determined by a perifusion protocol in three different human islet preparations, carried out under constant, physiologic glucose concentration. Groups of 100 handpicked islets (diameter 100-150 µm) cultured under control conditions for 4-7 days were perifused with KREBB containing 5.6 mmol/l glucose. During the 90 minute perifusion period, the SOD-mimic was added between minute 30 and 60. The insulin concentration of the elution samples was measured by ELISA (ALPCO).

Administration of SOD-Mimic During Islet Isolation

In the second series of experiments, SOD-mimic was administered during the isolation phase as well as during culture. The pancreatic lobe was divided in two parts (body and tail), of similar size (27±3 grams) randomly assigned to control and experimental conditions. During isolation SOD-mimic (concentration 34~mol/l) was delivered to the half of the pancreatic tissue together with Liberase™, by intra-ductal injection. In the control group, only Liberase™ was infused. The split organs are not amenable to automatic processing therefore stationary digestion was carried out in parallel on the two organ segments. The samples were digested for 30 minutes at 37° C. with periodic shaking Cell dissociation was finalized by manual teasing of the tissue. Cells and aggregates were filtered through a 500 µm mesh and collected in cold RPMI-1640 culture medium (Life Technologies) containing 10% heat-inactivated fetal calf serum. Prior to COBE processing, the pancreatic digests were incubated with cold UW solution with or without SOD-mimic (34 µmol/l) for 45 minutes. Purification and culture were then continued as described in the first series of experiments.

Islet Transplantation Under the Kidney Capsule of Diabetic Mice

Islets grafts of 200 to 1000 IEQ (islet equivalents) from four different organs, were cultured in the presence of SOD-mimic or kept in control conditions for at least two hours before transplantation. Streptozotocin-induced diabetic (Sigma, 250 mg/kg body weight) NOD-scid or Rag 1 mice (Jackson Laboratories, Bar Harbor, Me.) exhibiting non-fasting blood glucose levels of >300 mg/dl were used as recipients. Animals were anesthetized by I.P. injection of Avertin (0.30-0.40 mg/gram body weight). Control or SOD-treated islets were transplanted under the mouse kidney capsule (Alexander et al, *Diabetes* 51:356-365 (2002)). Successful engraftment was defined by reduction of glycemic levels to <200 mg/dl following transplantation. After 4 to 7 weeks post-transplantation, normalized recipients underwent nephrectomy to remove the islet graft. Return to hyperglycemia was interpreted as indirect proof of islet graft function.

Statistical Methods

Statistical analysis was carried out by Student's t test, Mann-Whitney nonparametric test, and Kaplan and Meier analysis. P values<0.05 were deemed statistically significant.

Results
Presence of SOD-Mimic Preserves Islet Cell Mass

Figure 14:
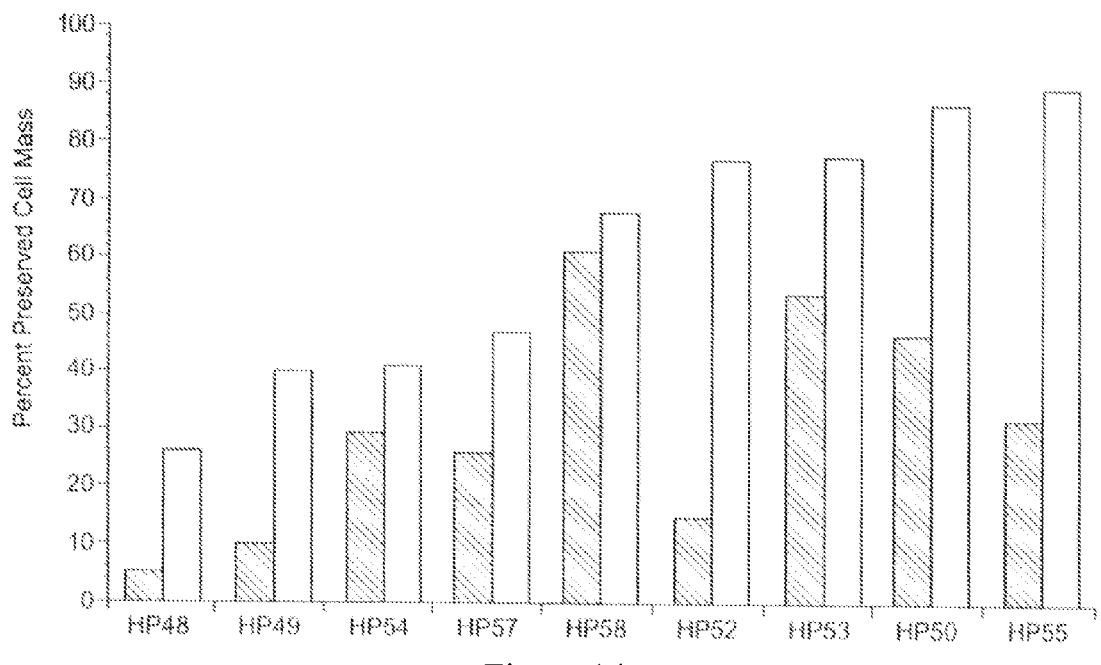
FIG. 14. Percentage of preserved islet cell mass between day 2-7 during culture, in control (closed bars) and SOD-mimic (open bars) treated groups (n=9). DNA content measured at day 2 (24 hours after isolation) has been arbitrarily considered as the starting reference value. Differences between groups were statistical significant (p=0.02; by Mann-Whitney test).

Isolated islets from nine donor pancreata, were divided into two groups and cultured either in CMRL-1066 alone or supplemented with SOD-mimic. The results in FIG. 14 demonstrate that in all experimental groups (n=9), a 3-fold mean increase in cell mass was observed when compared to controls (p=0.02). It should be noted that the difference in DNA content between control and experimental groups was appreciable starting from day 2 (24 hours after isolation) and steadily observed over the remaining culture period. However, in the first 24 hours of culture, a similar decrease in cell mass was observed in control and SOD-treated islet preparations accounting for 20-40% of the initial cell mass. These data demonstrate that addition of SOD-mimic reduces cell loss significantly over time, although it appears that there is no protective effect on those cells that die very early, within 24 hours following isolation.

Cell Viability

Double fluorescence viability was performed to determine whether DNA content might be affected by the presence of dead non-degraded cells in higher proportion within the SOD-mimic-treated preparations. The results indicate that in both control and SOD treated aggregates, a similar number of viable and dead cells was present, however, the islet number was higher in SOD-treated than in the control group. At a later stage of the culture period, control preparations showed higher dead cell contents, but the difference did not reach statistical significance (Table 2a).

Static Glucose Challenge and In Vitro Islet Function

Islet glucose responsiveness was assessed by a static glucose challenge method between days 3 and 5 after isolation (Table 2b). Upon glucose stimulation insulin release, expressed as absolute value or as a percentage of the insulin content and stimulation indices were similar, regardless of the culture treatment. Also basal insulin release did not differ between groups.

Also studied was the effect of addition of SOD-mimic on insulin release during a 90-minute perifusion protocol of isolated human islets (n=3) under constant glucose concentration. The results demonstrate that SOD-mimic supplementation does not affect insulin secretion. Basal release was similar in all groups, regardless of the addition of SOD-mimic to the medium.

TABLE 2

Islet functional properties a) Viability

| Groups | Culture day 1-4 | | Culture day 5-10 | |
| --- | --- | --- | --- | --- |
| | Viable % | Dead % | Viable % | Dead % |
| Control | 80 ± 5 | 2.0 ± 5 | 92 ± 5 | 8 ± 5 |
| SOD-mimic | 79 ± 5 | 21 ± 5 | 86 ± 5 | 14 ± 5 |

Percentage of viable and dead cells present in islet preparations (n = 9). Values are mean ± SEM.
Differences are not statistically significant.

b) In vitro glucose-responsiveness

| Groups | Stimulated insulin secretion µU | % Insulin | Stimulation index |
| --- | --- | --- | --- |
| Control | 13 ± 2 | 3 ± 1 | 5.5 ± 1.5 |
| SOD-mimic | 14 ± 2 | 3 ± 0.5 | 5.8 ± 1 |

Stimulated insulin secretion values are obtained by subtracting basal from 20 mmol/l glucose-induced insulin release.
Values are mean ± SEM of five (n = 5) islet preparations.

Characterization of the Total Cell Mass

Figures 15A, 15B:
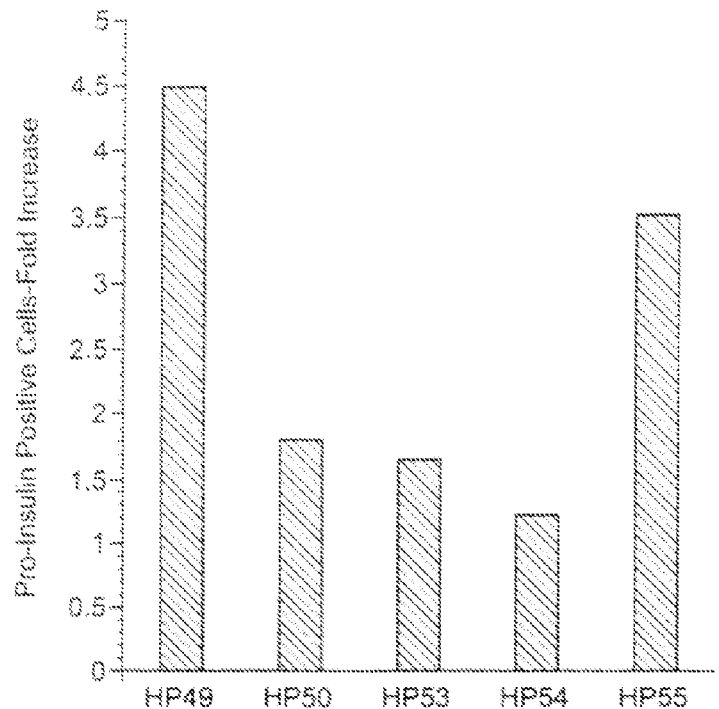
FIGS. 15A and B. A) Immunocytochemical characterization of islet preparations from five human pancreata before and after culture. The number of positive cells was counted and expressed as percentage of the total. The percentage of pro-insulin positive cells was maintained over the culture period in all preparations irrespective of the treatment. After culture, a statistically significant (*p<0.01; by t test) decrease in amylase positive cells was observed in both control and SOD-mimic treated preparations. B) Bar graphs show the fold-increase in preserved beta cell mass in SOD-mimic-treated preparations compared to control over the culture time. Beta cell mass was calculated by combining DNA content as indicator of cell number with immunocytochemical analysis (Keymeulen et al, *Diabetologia* 41:452-459 (1998)).

To exclude the possibility that higher DNA contents in SOD-treated preparations could be attributed to selective survival of non-islet tissue, the islets preparations (n=5) were characterized by immunocytochemistry. The relative proportion of pro-insulin (beta cells), glucagon (alpha cells), amylase (exocrine), and CK19 (ductal cells) was determined (FIG. 15A). In all cases, cell composition was minimally different between SOD-mimic-treated and control groups. Both groups showed a reduction in amylase immuno-reactive cells that changed from values as large as 20% at start, to negligible values after culture, regardless of the culture treatment (p<0.01). When the proportion of pro-insulin positive cells (% of beta cells) was expressed as a fraction of DNA content, used as an indicator of cell number, the results demonstrate that SOD-mimic treatment accounts for a minimum 1.3 to a maximum of 4.5 fold increase in beta cell mass (FIG. 15B). These data demonstrate that treatment of islets with SOD increases overall beta cell mass without appreciable dysregulation in islet function.

Early Administration of SOD-Mimic Reduces Cell Loss

Figure 16:
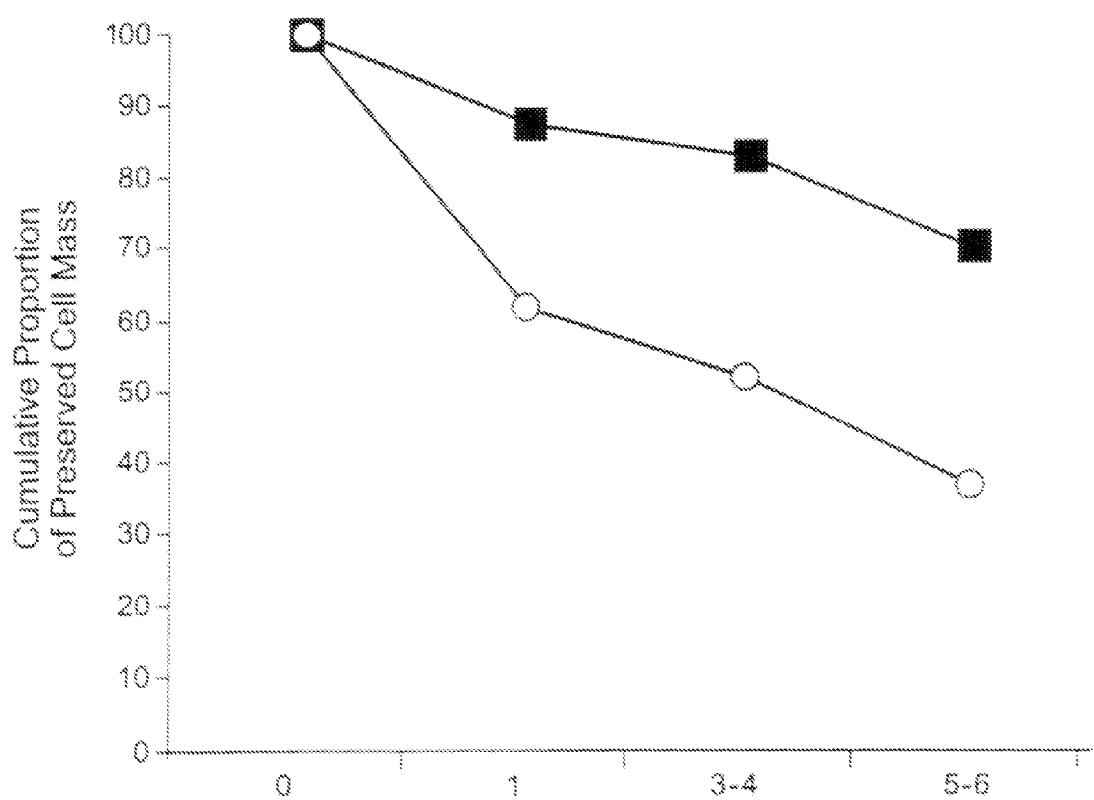
FIG. 16. Survival rate for islet preparations of the SOD-mimic group: —and Control group: —The donor pancreata (n=3) were divided in two fractions and treated with or without SOD-mimic during isolation. From the Kaplan and Meier analysis, it can be inferred that islet cell loss reduced in SOD-treated pancreatic tissue as compared to control tissue (log rank, p=0.0001). Remarkably this difference was seen after 24 hours.

The aim of the three additional experiments was to determine whether administration of SOD-mimic during the digestion might play a more protective role on cell survival than its addition in culture after isolation. To avoid the impact of donor variables on the quality of the isolated islets, the technical approach of splitting the organs in two parts has been adopted. After infusion of Liberase™ solution with or without SOD-mimic, an arbitrary incubation time of 30 minutes was maintained in all groups. Importantly, the presence of SOD-mimic did not appear to affect the digestion duration. Treated and control preparations for each donor organ yielded islet fractions of similar purity. FIG. 16 demonstrates the relative variations in DNA content of control and experimental islet preparations following isolation. The data indicate that in all three cases, a significant (p=0.0001) increase in islet cell mass was appreciable 24 hours post isolation in the SOD-treated organs, and that the difference was maintained over time. Treated and control islets were tested for viability and functional capacity in vitro. In both cases more than 80% of viable cells were counted among the islet preparation samples with no difference associated with the treatment. The values of insulin content, basal and stimulated insulin release per islet was also not different between the two groups. This demonstrates that the addition of the SOD-mimic during digestion resulted in greater numbers of functional islets with respect to controls.

Normalization of Diabetic Mice

Figure 17A:
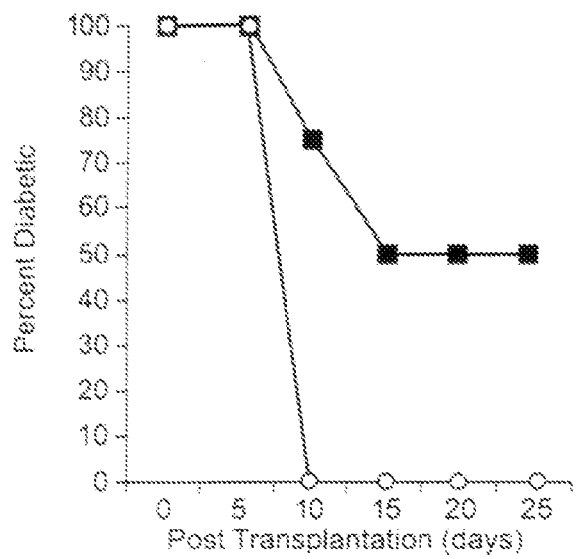
FIGS. 17A-C. Metabolic capacity of islet grafts in vivo. Glycemia normalization time following islet transplantation of variable islet mass: A) Islet grafts: 200-220 IEQ. Control n=4, SOD-mimic n=5. B) Islet grafts: ~400 IEQ Control n=4, SOD-mimic n=4. C) Islet grafts: 700-1000 IEQ Control n=3, SOD-mimic n=3. —black triangles—Control; —white circles—SOD-mimic.
Figure 17B:
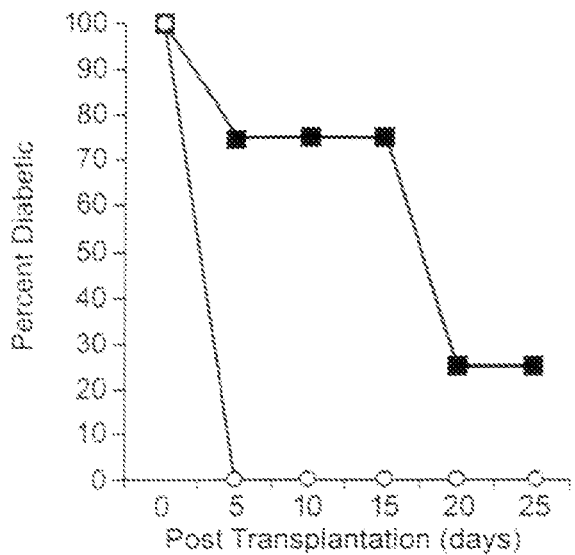
Figure 17C:
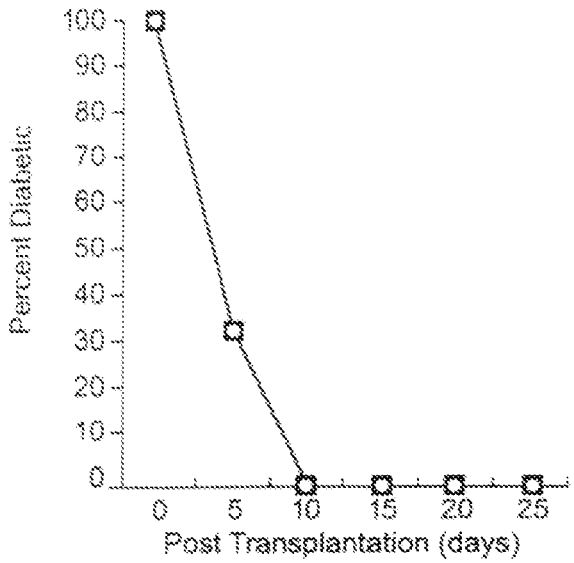
Figure 18D:
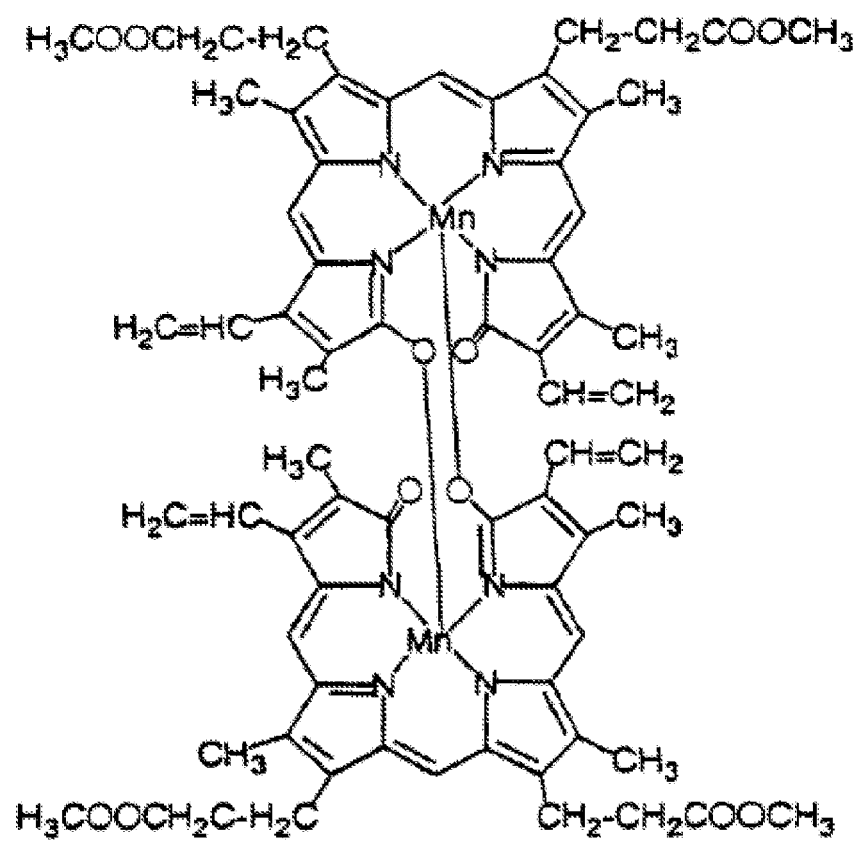
Figure 18E:
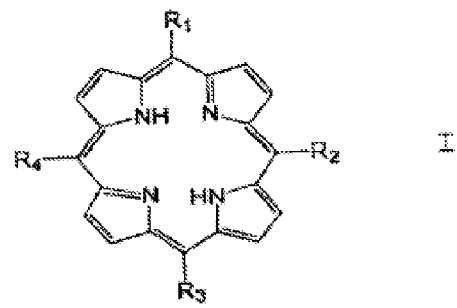
Figure 18E:
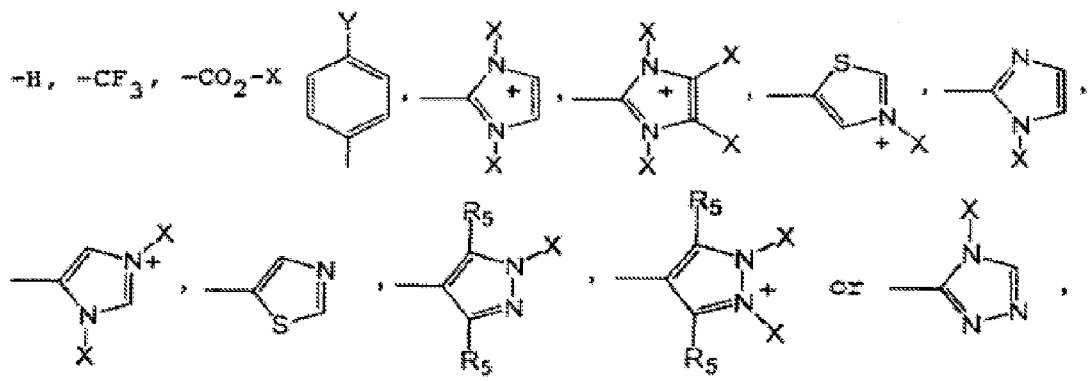
Figure 18E:
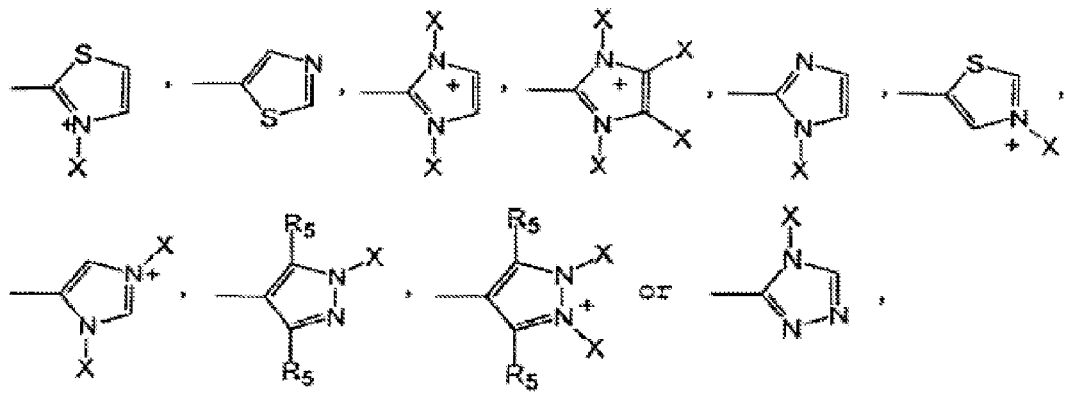
Figure 18G:
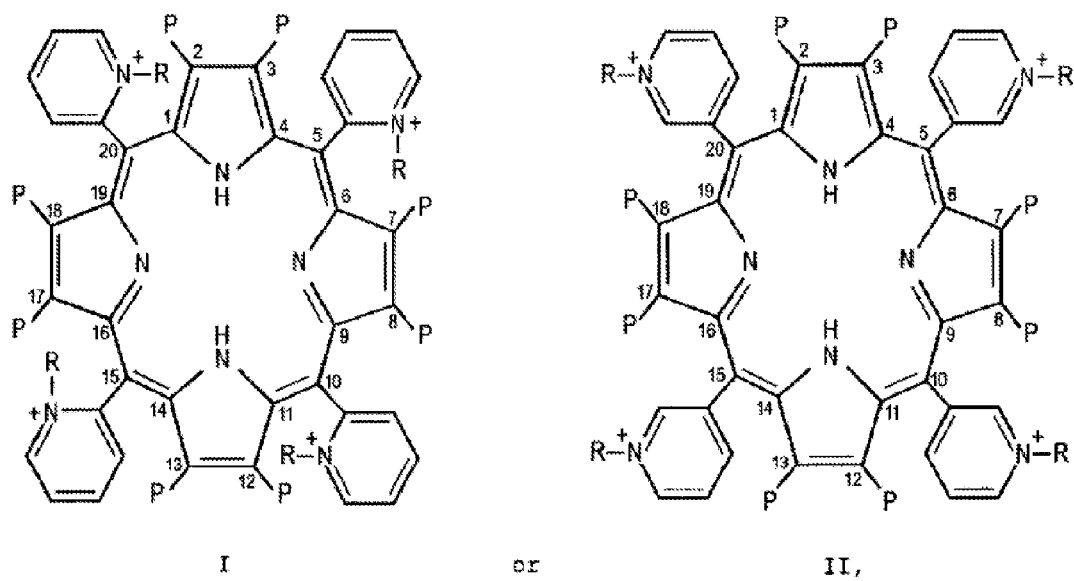
Figure 18H:
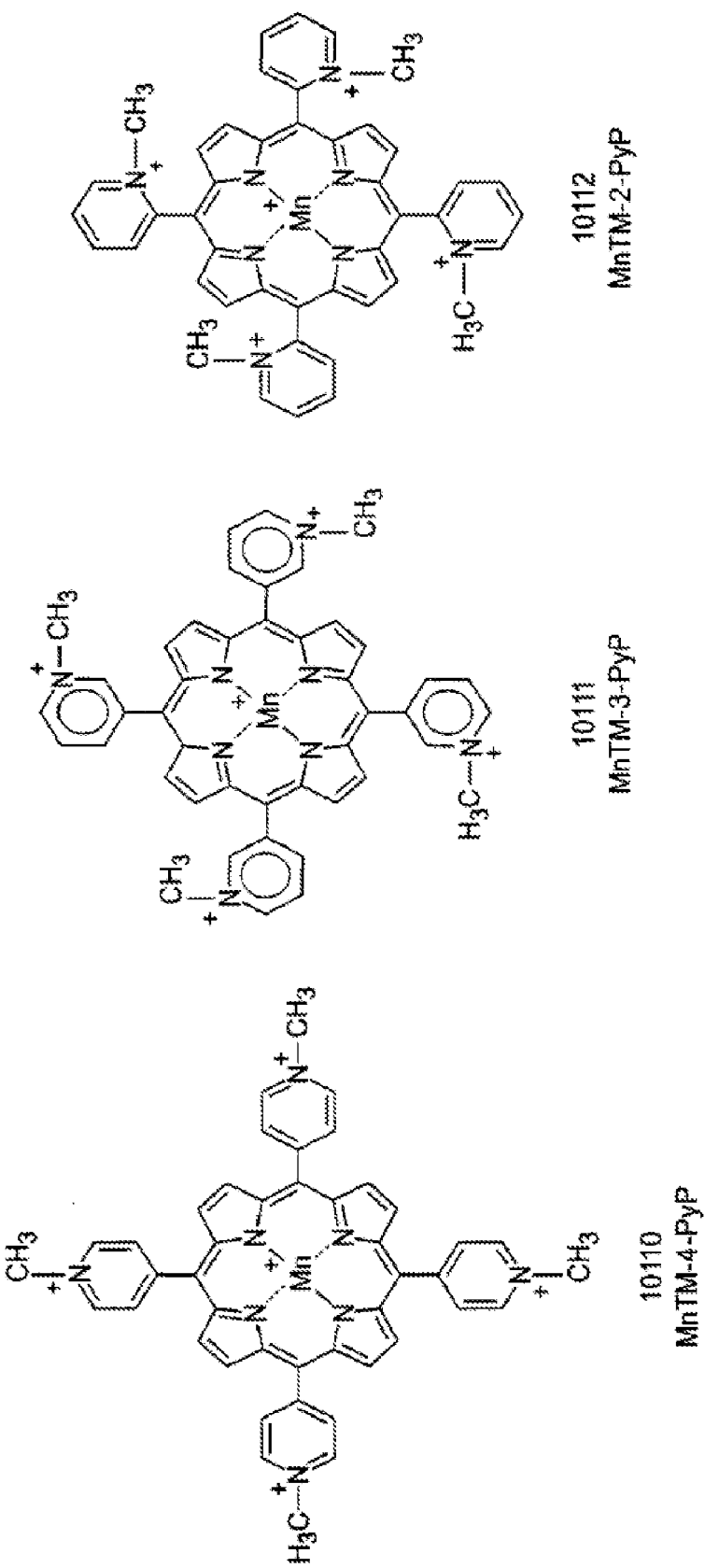
Figure 18I:
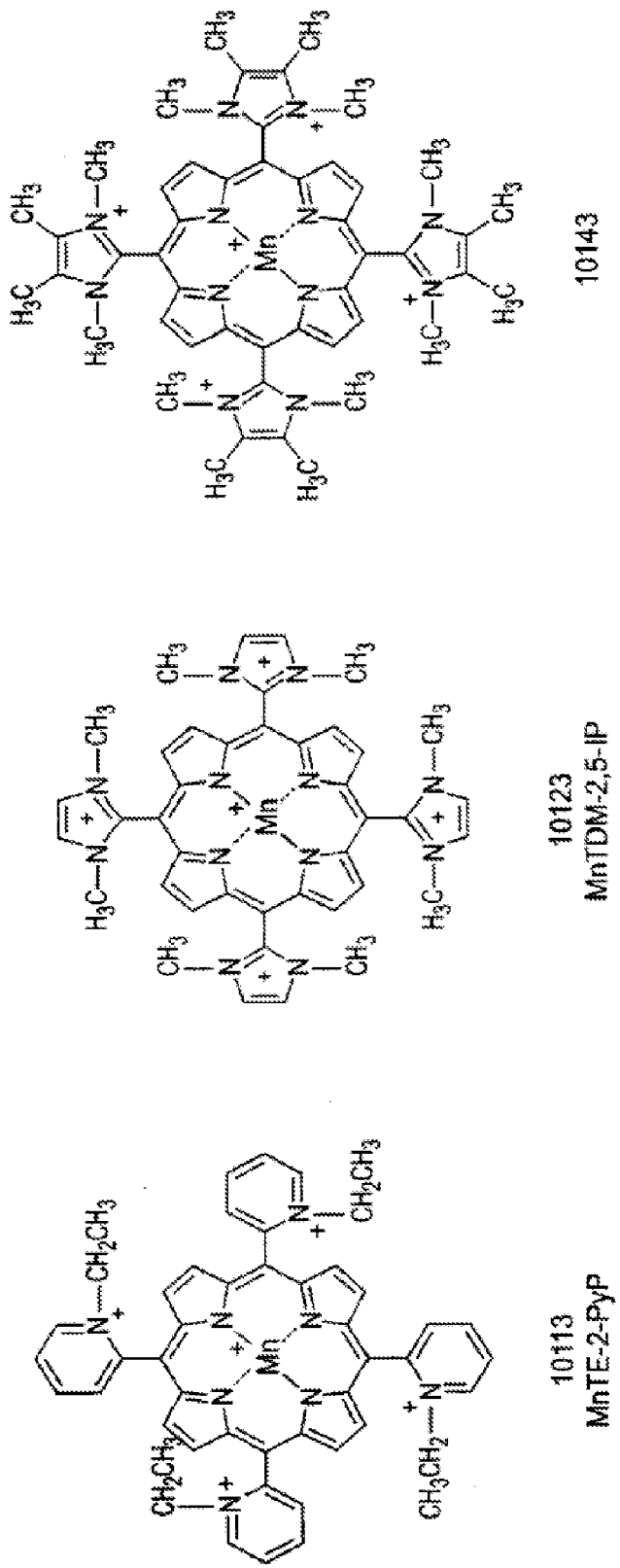
Figure 18J:
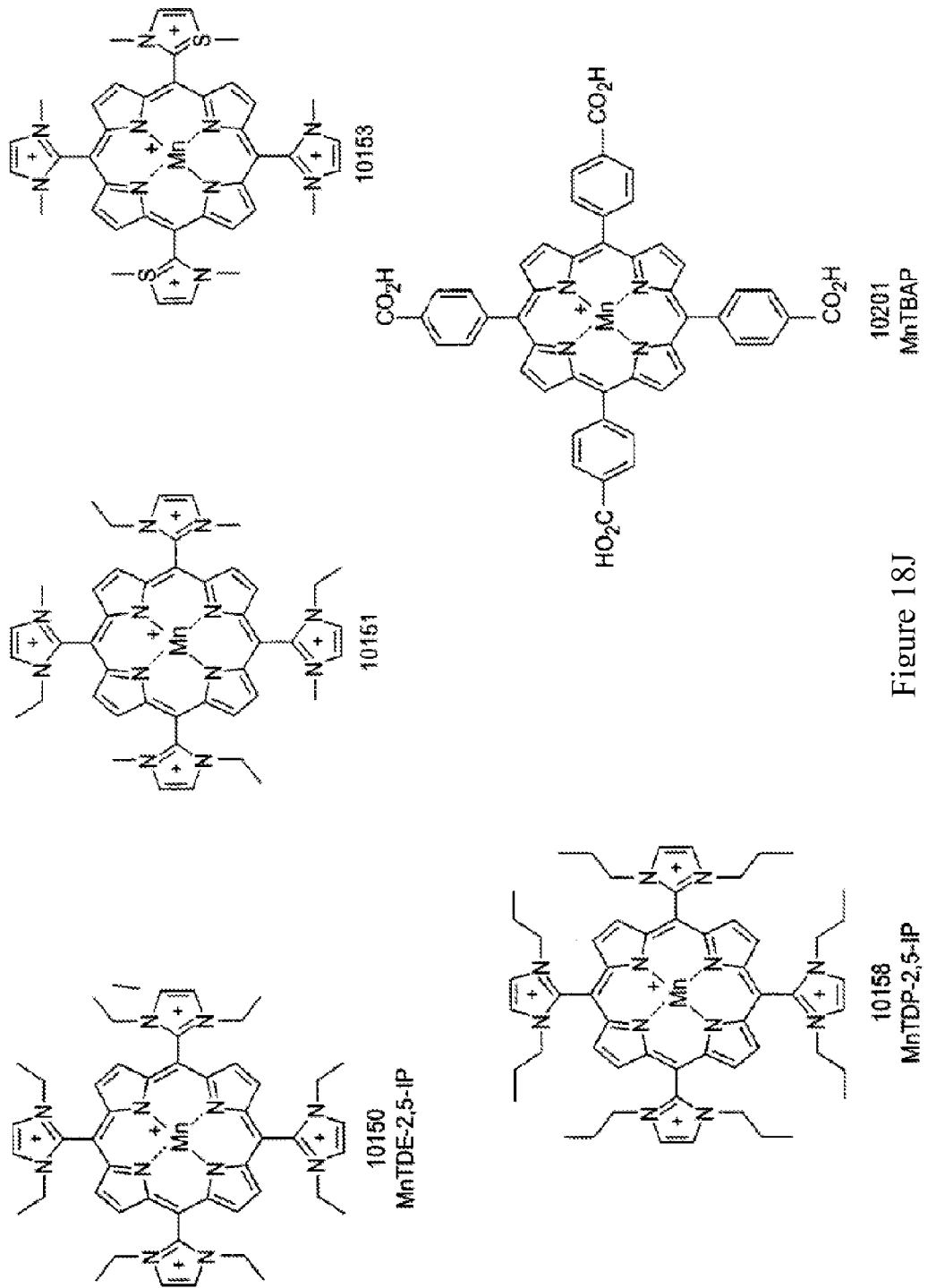
Figure 18K:
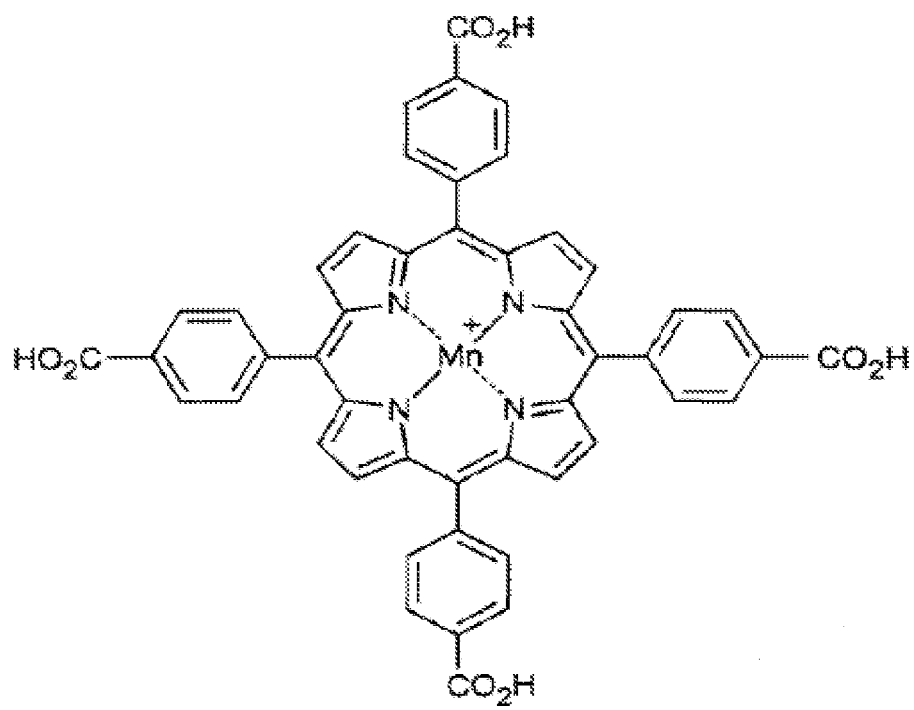

Diabetic recipient mice were randomly assigned to receive islet transplants from control and SOD-mimic treated groups (FIG. 17). The first three recipients of each group received an islet mass of 700 to 1000 IEQ. All six recipients normalized the glucose levels within the first week of the post-transplant period. When the number of transplanted islets was reduced to less than 400 IEQ per graft, all recipients (n=9) of SOD-treated islets normalized, while in the control group, three recipients of islet grafts (respectively composed of 200, 220, and 400 IEQ) never corrected glucose levels. In all successful transplants, animals maintained normoglycemia for more than 30 days. In the cases in which the graft was removed by nephrectomy, all mice return to hyperglycemic state.

All documents cited above are hereby incorporated in their entirety by reference.

What is claimed is:

1. A method of treating type I diabetes or type II diabetes, said method comprising administering to a patient in need an effective amount of a compound of formula

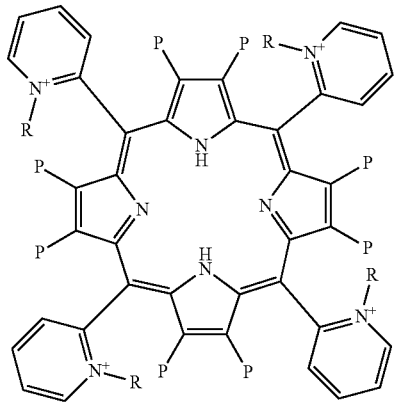

or pharmaceutically acceptable salt thereof,
wherein
each R is independently $C_{1-8}$ alkyl, and
each P is independently an electron withdrawing group or hydrogen.

2. The method according to claim 1, wherein said compound is complexed with a metal selected from the group consisting of manganese, iron copper, cobalt, nickel and zinc.

3. The method according to claim 2, wherein said metal is manganese.

4. The method according to claim 1, wherein said electronic withdrawing group is alkyl, 2-hydroxyalkyl, methoxyalkyl, halogen, nitro, cyano, trialkylammonium, formyl, amide of carboxylic acid, alkyl ester of carboxylic acid, carboxylic acid, glucuronyl or glyceryl ester of carboxylic acid, 1,2-dihydroxyalkyl, acetyl, vinyl, glycosyl or taurate.

5. The method according to claim 1, wherein each P is hydrogen.

6. The method according to claim 1, wherein each R is $C_6$ alkyl.

7. The method according to claim 1, said compound of formula

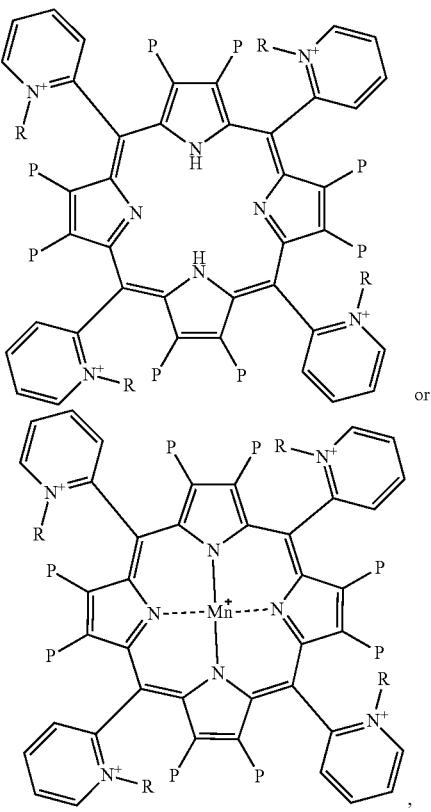

or pharmaceutically acceptable salt thereof,
wherein
each R is independently $C_6$ alkyl, and
each P is independently hydrogen.

8. The method according to claim 7, wherein said diabetes results from death of pancreatic islet cells due to autoimmune disease.

9. The method according to claim 7, wherein said diabetes results from death of pancreatic islet cells due to radical induced toxicity.

* * * * *